United States Patent
Sudhakar et al.

(10) Patent No.: US 11,045,481 B2
(45) Date of Patent: Jun. 29, 2021

(54) QUETIAPINE ORAL LIQUID SUSPENSION AND USE THEREOF

(71) Applicant: OWP Pharmaceuticals, Inc., Naperville, IL (US)

(72) Inventors: Paul Sudhakar, Shawnee, KS (US); Scott Boyer, West Chicago, IL (US)

( * ) Notice: Subject to any disclaimer, the term of this patent is extended or adjusted under 35 U.S.C. 154(b) by 0 days.

(21) Appl. No.: 17/083,497

(22) Filed: Oct. 29, 2020

(65) Prior Publication Data

US 2021/0121477 A1    Apr. 29, 2021

Related U.S. Application Data

(60) Provisional application No. 62/927,153, filed on Oct. 29, 2019.

(51) Int. Cl.
| | | |
|---|---|---|
| *A61K 31/554* | (2006.01) | |
| *A61K 47/14* | (2017.01) | |
| *A61K 47/12* | (2006.01) | |
| *A61K 47/26* | (2006.01) | |
| *A61K 47/24* | (2006.01) | |
| *A61P 25/18* | (2006.01) | |
| *A61K 47/38* | (2006.01) | |
| *A61K 47/36* | (2006.01) | |
| *A61K 47/34* | (2017.01) | |
| *A61K 9/00* | (2006.01) | |
| *A61K 9/14* | (2006.01) | |
| *A61K 47/10* | (2017.01) | |

(52) U.S. Cl.
CPC .......... *A61K 31/554* (2013.01); *A61K 9/0053* (2013.01); *A61K 9/14* (2013.01); *A61K 47/10* (2013.01); *A61K 47/12* (2013.01); *A61K 47/14* (2013.01); *A61K 47/24* (2013.01); *A61K 47/26* (2013.01); *A61K 47/34* (2013.01); *A61K 47/36* (2013.01); *A61K 47/38* (2013.01); *A61P 25/18* (2018.01)

(58) Field of Classification Search
CPC ...... A61K 31/554; A61K 9/0053; A61K 9/14; A61K 47/10; A61K 47/12; A61K 47/14; A61K 47/24; A61K 47/26; A61K 47/34; A61K 47/36; A61K 47/38; A61P 25/18
See application file for complete search history.

(56) References Cited

U.S. PATENT DOCUMENTS

| | | | | |
|---|---|---|---|---|
| 9,993,486 | B1 * | 6/2018 | Tierney | ............ B65B 7/28 |
| 10,561,669 | B2 * | 2/2020 | Tierney | ......... A61K 9/0095 |
| 2018/0360844 | A1 * | 12/2018 | Tierney | .......... A61K 47/24 |
| 2019/0154648 | A1 * | 5/2019 | Lawrence | ........ A61K 9/0046 |
| 2020/0179399 | A1 * | 6/2020 | Tierney | .......... A61K 47/24 |

\* cited by examiner

*Primary Examiner* — Robert A Wax
*Assistant Examiner* — Olga V. Tcherkasskaya
(74) *Attorney, Agent, or Firm* — Carlson, Caspers, Vandenburgh & Lindquist, P.A.

(57) ABSTRACT

The present invention provides for an oral liquid suspension that includes quetiapine or a pharmaceutically acceptable salt thereof. Also provided is a method for orally delivering quetiapine fumarate to a subject (e.g., for treating a mental disorder in a subject, such as schizophrenia, bipolar mania, and/or bipolar depression). The method includes orally administering to the subject an oral liquid suspension described herein.

26 Claims, No Drawings

QUETIAPINE ORAL LIQUID SUSPENSION AND USE THEREOF

RELATED U.S. APPLICATION DATA

This application claims priority to U.S. provisional patent application No. 62/927,153 filed on Oct. 29, 2019; the contents of which are incorporated by reference herein in its entirety.

SUMMARY OF THE INVENTION

The present invention provides for an oral liquid suspension that includes quetiapine or a pharmaceutically acceptable salt thereof, preservative, sweetening agent, pH modifying agent, solvent, viscosity-increasing agent, suspending agent, and surfactant.

The present invention also provides for an oral liquid suspension that includes: quetiapine or a pharmaceutically acceptable salt thereof; sodium benzoate powder; saccharin sodium dihydrate powder; sodium phosphate dibasic; sorbitol solution 70%; propylene glycol; glycerin 99.7% natural grade; the product microcrystalline cellulose (MCC) and colloidal silicon dioxide (CSD) sold under the trademark PROSOLV® SMCC 50; carboxymethylcellulose sodium, medium viscosity (2% aqueous solution at 25° C. is 400 cps to 800 cps); xanthan gum; purified water; poloxamer 188 (2-(2-propoxypropoxy)ethanol); polyethylene glycol 400; and sucralose.

The present invention also provides for an oral liquid suspension that includes: quetiapine fumarate, present in an amount equal to 25 mg/ml quetiapine (i.e., 28.75 mg/ml quetiapine fumarate); methylparaben, present in 1 mg/ml; sodium benzoate powder, present in 0.3 mg/ml; saccharin sodium dihydrate powder, present in 0.8 mg/ml; sodium phosphate dibasic, present in 0.3 mg/ml; sorbitol solution 70%, present in 30 mg/ml; propylene glycol, present in 22.5 mg/ml; glycerin 99.7% natural grade, present in 50 mg/ml; the product microsrystalline cellulose (MCC) and colloidal silicon dioxide (CSD) sold under the trademark PROSOLV@ SMCC 50, present in 12.6 mg/ml; carboxymethylcellulose sodium, medium viscosity (2% aqueous solution at 25° C. is 400 cps to 800 cps), present in 1.8 mg/ml; xanthan gum, present in 1.8 mg/ml; purified water, present in 787.046 mg/ml; poloxamer 188 (2-(2-propoxypropoxy) ethanol), present in 6 mg/ml; polyethylene glycol 400, present in 50 mg/ml; and sucralose, present in 5 mg/ml.

The present invention also provides for an oral liquid suspension that includes:

| % W/V | Material/Component |
|---|---|
| 28.83 mg/ml | quetiapine fumarate |
| 1 mg/ml | methylparaben |
| 0.3 mg/ml | sodium benzoate powder |
| 0.8 mg/ml | saccharin sodium dihydrate powder |
| 0.3 mg/ml | sodium phosphate dibasic |
| 30 mg/ml | sorbitol solution 70% |
| 22.5 mg/ml | propylene glycol |
| 50 mg/ml | glycerin 99.7% natural grade |
| 12.6 mg/ml | PROSOLV ® SMCC 50 (silicified microcrystalline cellulose) |
| 1.8 mg/ml | carboxymethylcellulose sodium, medium viscosity (2% aqueous solution at 25° C. is 400-800 cps) |
| 1.8 mg/ml | xanthan gum |
| 787.046 mg/ml | purified water |
| 6 mg/ml | Poloxamer 188 (2-(2-propoxypropoxy)ethanol) |
| 50 mg/ml | polyethylene glycol 400 |
| 5 mg/ml | sucralose |
| 2.00 mg/ml | cherry flavor (natural and artificial) |
| 0.02 mg/ml | FD&C red #40 |
| 0.002 mg/ml | FD&C yellow #6 |
| TOTAL 998.198 mg/ml | |

The present invention also provides for a method for orally delivering quetiapine fumarate to a subject. The method includes administering to the subject an oral liquid suspension described herein.

The present invention also provides for a method for treating a mental disorder in a subject. The method includes orally administering to a subject suffering from the disorder an effective amount of an oral liquid suspension described herein.

The present invention also provides for a method for treating at least one of the disorders (i) schizophrenia in an adult; (ii) schizophrenia in an adolescent (13-17 years); (iii) bipolar mania in an adult, monotherapy or as an adjunct to lithium or divalproex; (iv) bipolar mania in a children or adolescent (10-17 years), monotherapy; and (v) bipolar depression in adults. The method includes administering to a subject suffering from the disorder(s) an effective amount of an oral liquid suspension described herein.

DETAILED DESCRIPTION OF THE INVENTION

The present invention can be more readily understood by reading the following detailed description of the invention and study of the included examples.

The present invention is based, in part, upon the discovery of novel oral liquid suspensions that provide advantages when used for the in vivo delivery to a mammal of the active pharmaceutical ingredient (API) quetiapine fumarate. In doing so, the present invention provides for oral liquid suspensions that provide for a suitable therapeutic index and optionally a lower incidence, severity, and/or duration of adverse reaction(s) compared to previously described dosage forms containing the active ingredient in the same amount.

The oral liquid suspensions may be used for a variety of purposes, including for the in vivo delivery of the active pharmaceutical ingredient quetiapine, or pharmaceutically acceptable salty thereof. Accordingly, the present invention further provides a method of treating diseases or disorders such as psychiatric diseases and disorders (e.g., Schizophrenia, Bipolar I disorder manic episodes, and/or Bipolar disorder depressive episodes).

Relative to oral tablets containing an equivalent amount of quetiapine fumarate, administration of the oral liquid suspension described herein in specific embodiments can result in a lower incidence, severity, and/or duration of adverse reactions including at least one of hyperglycemia, dyslipidemia, somnolence, dry mouth, dizziness, constipation, asthenia, abdominal pain, postural hypotension, pharyngitis, weight gain, lethargy, alanine aminotransferase (ALT) increased, dyspepsia, fatigue, increased appetite, nausea, vomiting, and tachycardia.

In forming an oral liquid suspension, any one or more of the excipients employed can effectively be dissolved or dispersed therein (e.g., in the solvent). This includes, e.g., salts, such as sodium benzoate, saccharin sodium, and sodium carboxymethyl cellulose. In doing so, the salt can dissociate into the respective anion and cation; and would therefore no longer necessarily exist in the salt form-benzoic acid, saccharin, and carboxymethyl cellulose. However, within the context of the invention, it is appreciated that those of skill in the art understand and agree that reference to the oral liquid suspension as containing the salt form is otherwise acceptable and appropriate.

Likewise, in specific embodiments, the drug, substance quetiapine fumarate, having a specified particle size distribution (PSD), can be employed in the manufacture of the drug product, oral liquid suspension. In forming the oral liquid suspension, the quetiapine fumarate present can effectively be suspended and/or dissolved therein (e.g., in the solvent). In doing so, the quetiapine fumarate would therefore no longer necessarily retain the drug substance PSD. However, within the context of the invention, it is appreciated that those of skill in the art understand and agree that reference to the oral liquid suspension as containing the quetiapine fumarate as having a specified PSD (based on the drug substance quetiapine fumarate employed) is otherwise acceptable and appropriate. Alternatively, reference to the oral liquid suspension as containing the quetiapine fumarate as having a specified PSD (based on the drug substance quetiapine fumarate present in the oral liquid suspension) is also acceptable and appropriate. As such, the PSD of the drug substance quetiapine fumarate employed is often a parameter for the PSD of quetiapine fumarate present in the oral liquid suspension.

As used herein, "oral liquid suspension comprising" or "oral liquid suspension that includes" refers to an oral liquid suspension manufactured from the specified ingredients. While the oral liquid suspension may include such ingredients, it is appreciated that those of skill in the art understand that one or more of the specified substances may not exist in that form, within the oral liquid suspension. However, reference to the oral liquid suspension as containing that substance is otherwise acceptable. By way of illustration, a powder may fully dissolve in the oral liquid suspension. As such, the powder form may no longer exist in the oral liquid suspension. However, reference to the oral liquid suspension as containing a powder is readily understood by the skilled artisan.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "excipient" refers to a pharmacologically inactive component present in the oral liquid suspension. Excipients include, e.g., preservatives, sweetening agents, solvents, anticaking agents, viscosity-increasing agents, suspending agents, surfactants, acidifying agents, flavoring agents, and colorants. The excipients used in preparing the oral liquid suspension described herein are safe and non-toxic. Suitable excipients are disclosed in Handbook of Pharmaceutical Excipients, Rowe et al., Eds., 8th Edition, Pharmaceutical Press (2017).

One or more excipients employed in the oral liquid suspensions described herein can have a single use. For example, when present in the oral liquid suspension described herein, methylparaben can function as a preservative; saccharin sodium dihydrate powder, sucralose, and sorbitol can each function as a sweetening agent; quetiapine fumarate can function as an active pharmaceutical ingredient; sodium benzoate can function as a preservative; disodium phosphate can function as a pH modifying agent; cherry flavor (natural and artificial) can function as a flavoring agent; and/or FD&C red #40 and FD&C yellow #6 can function as a colorant.

Additionally, one or more excipients employed in the oral liquid suspensions described herein can have a single or multiple uses. For example, microcrystalline cellulose can function as a suspending agent, texturizer, anti-caking agent, or any combination thereof; propylene glycol can function as a preservative, solvent, viscosity-increasing agent, or any combination thereof; polyethylene glycol can function as a solvent, viscosity-increasing agent, suspending agent, or any combination thereof; glycerin can function as a preservative, sweetening agent, solvent, viscosity-increasing agent, or any combination thereof; xanthan gum can function as a viscosity-increasing agent, suspending agent, or a combination thereof; and/or poloxamer 188 can function as a surfactant, emulsifying agent, solubilizing agent, dispersing agent, or any combination thereof.

In specific embodiments, the present invention provides for an oral liquid suspension that includes quetiapine or a pharmaceutically acceptable salt thereof, preservative, sweetening agent, pH modifying agent, solvent, viscosity-increasing agent, suspending agent, viscosity-increasing agent, and surfactant. It is contemplated that one or more excipients can be employed in the oral liquid suspension to effectively serve multiple functions. Specifically, a single excipient can function as a preservative, solvent, and viscosity-increasing agent. Further, a single excipient can function as a preservative, sweetening agent, solvent, and viscosity-increasing agent. Excipients useful in the oral liquid suspensions described herein, having multiple functions, are described in Handbook of Pharmaceutical Excipients, Rowe et al., Eds., 8th Edition, Pharmaceutical Press (2017).

The term "preservative" refers to a substance that is added to products, such as oral liquid suspensions, to prevent decomposition by microbial growth or by undesirable chemical changes. In general, preservation is implemented in two modes, chemical and physical. Suitable preservatives include, e.g., one or more of ethanol, benzoic acid, benzyl alcohol, bronopol, butylated hydroxyanisole (BHA), butylparaben, calcium acetate, calcium chloride, calcium lactate, cetrimide, cetylpyridinium chloride, chlorhexidine, chlorobutanol, chlorocresol, chloroxylenol, citric acid monohydrate, ethylparaben, glycerin, hexetidine, imidurea, isopropyl alcohol, lactic acid, methylparaben, monothioglycerol, parabens, pentetic acid, phenoxyethanol, phenylethyl alcohol, potassium benzoate, potassium metabisulfite, potassium sorbate, propionic acid, propyl gallate, propylene glycol, propylparaben, propylparaben sodium, sodium acetate, sodium benzoate, sodium borate, sodium lactate, sodium metabisulfite, sodium propionate, sodium sulfite, sorbic acid, sulfobutyl ether β-cyclodextrin, edetic acid, thimerosal, and xanthan.

The term "sweetening agent" or "sweetener" refers to a substance that is added to products, such as oral liquid suspensions, to provide a sweet taste like that of sugar. The sweetener can include, e.g., one or more of acesulfame potassium, alitame, aspartame, dextrose, erythritol, fructose, glycerin, isomalt, lactitol, glucose, maltitol, maltose, mannitol, monk fruit extract, neohesperidin dihydrochalcone, neotame, saccharin, saccharin sodium, sodium cyclamate, sorbitol, stevia, sucralose, sucrose, tagatose, thaumatin, trehalose, and xylitol.

The term "solvent" refers to a substance that is added to products, such as oral liquid suspensions, to dissolve the active pharmaceutical ingredient and/or excipients. The solvent can include, e.g., one or more of albumin, ethanol, almond oil, benzyl alcohol, benzyl benzoate, butylene glycol, castor oil, corn oil (maize), cottonseed oil, dimethyl ether, dimethylacetamide, ethyl lactate, ethyl oleate, glycerin, isopropyl alcohol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl castor oil, propylene carbonate, propylene glycol, pyrrolidone, safflower oil, sesame oil, soybean oil, sunflower oil, triacetin, tricaprylin, triethanolamine, triethyl citrate, triolein, and water.

The term "surfactant" refers to a substance that that lower the surface tension (or interfacial tension) between two liquids or between a liquid and a solid. Surfactants may act as detergents, wetting agents, emulsifiers, foaming agents, or dispersants. The surfactant can include, e.g., Poloxamer 188.

The term "anticaking agent" refers to a substance that is added to products, such as oral liquid suspensions, to prevent or decrease the occurrence of agglomeration of particles, such as the active pharmaceutical ingredient and/or excipients. The anticaking agent is added to prevent or decrease the formation of lumps (caking), which provides for ease in packaging, transport, flowability, and consumption. The anticaking agent can include, e.g., one or more of tribasic calcium phosphate, calcium silicate, colloidal silicon dioxide, hydrophobic colloidal silica, magnesium oxide, magnesium silicate, magnesium trisilicate, and talc.

The term "viscosity-increasing agent" refers to a substance that is added to products, such as oral liquid suspensions, to increase the viscosity. The viscosity increasing agent is used in order to impart an appropriate viscosity to the oral liquid suspension. The viscosity increasing agent increases the viscosity of the oral liquid suspension without substantially changing its other properties. The viscosity-increasing agent can include, e.g., one or more of acacia, agar, alginic acid, bentonite, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, guar gum, hectorite, hydrogenated vegetable oil type I, hydrophobic colloidal silica, hydroxyethyl cellulose, hydroxyethylmethyl cellulose, hydroxypropyl cellulose, hydroxypropyl starch, hypromellose, magnesium aluminum silicate, maltodextrin, methylcellulose, myristyl alcohol, polydextrose, polyethylene glycol, polyvinyl alcohol, potassium chloride, povidone, propylene glycol alginate, saponite, sodium alginate, sodium chloride, starch, stearyl alcohol, sucrose, sulfobutyl ether β-cyclodextrin, tragacanth, and xanthan gum.

The term "suspending agent" refers to a substance that helps the active pharmaceutical ingredient stay suspended in the oral liquid suspension and prevents caking at the bottom of the container. One of the properties of a well-formulated oral liquid suspension is that it can be easily re-suspended by the use of moderate agitation or shaking. The suspending agent can include, e.g., one or more of acacia, agar, alginic acid, bentonite, calcium stearate, carbomers, carboxymethylcellulose calcium, carboxymethylcellulose sodium, carrageenan, powdered cellulose, cellulose, microcrystalline cellulose, carboxymethylcellulose sodium, ceratonia, colloidal silicon dioxide, dextrin, gelatin, guar gum, hectorite, hydrophobic colloidal silica, hydroxyethyl cellulose, hydroxyethylmethyl cellulose, hydroxypropyl cellulose, hypromellose, kaolin, magnesium aluminum silicate, maltitol solution, medium-chain triglycerides, methylcellulose, silicified microcrystalline cellulose, phospholipids, polycarbophil, polyethylene glycol, polyoxyethylene sorbitan fatty acid esters, potassium alginate, povidone, propylene glycol alginate, saponite, sesame oil, sodium alginate, sodium starch glycolate, sorbitan esters, sucrose, tragacanth, vitamin E polyethylene glycol succinate, and xanthan gum. Additionally, the suspending agent can include, e.g., the product microcrystalline cellulose (MCC) and colloidal silicon dioxide (CSD) sold under the trademark PROSOLV@ SMCC 50M.

The suspending agent is able to reduce the formation of quetiapine fumarate hydrate. In some embodiments, less than about 8 wt. %, less than about 5 wt. %, less than about 3 wt. %, less than about 1 wt. %, or less than about 0.5 wt. % of the quetiapine fumarate thereof is converted into its hydrate form over the period of time of manufacturing, shipping, and storage of the oral liquid suspension described herein (e.g., up to 6-9 months) under ambient conditions.

The suspending agent also contributes to the stability of the suspension after reconstitution. In some embodiments, less than about 5 wt. %, less than about 3 wt. %, less than about 1 wt. %, less than about 0.5 wt. %, less than about 0.2 wt. %, or less than about 0.1 wt. % of the quetiapine fumarate is decomposed over the period of time of manufacturing, shipping, and storage of the oral liquid suspension described herein (e.g., up to 6-9 months) under ambient conditions.

The term "acidifying agent" refers to a substance that is added to products, such as oral liquid suspensions, to lower the pH, or is added to achieve a desired pH that is lower than it would otherwise be in the absence of the acidifying agent. The acidifying agent can include, e.g., one or more of sodium phosphate dibasic, adipic acid, ammonium chloride, citric acid monohydrate, diluted hydrochloric acid, lactic acid, propionic acid, and tartaric acid.

The term "flavoring agent" refers to a substance that gives another substance flavor, altering the characteristics of the solute, causing it to become sweet, sour, tangy, etc. A flavor is a quality of something that affects the sense of taste. The flavoring agent can include, e.g., cherry flavor, grape, or peppermint.

The term "colorant" or "coloring agent" refers to substance that is added or applied in order to change the color of a material or surface. Colorants work by absorbing varying amounts of light at different wavelengths (or frequencies) of its spectrum, transmitting (if translucent) or reflecting the remaining light in straight lines or scattered. The colorant can include, e.g., FD&C red #40, FD&C yellow #6, or a combination thereof.

The term "oral liquid suspension" refers to a pharmaceutical dosage form that is a liquid and is orally administered. It includes quetiapine, or a pharmaceutically acceptable salt thereof (e.g., quetiapine fumarate) mixed with a liquid vehicle for oral administration. Being a suspension, the dosage form consists of undissolved particles (e.g., quetiapine fumarate and/or excipients). The undissolved particles can be suspended in the oral liquid suspension. Alternatively, the undissolved particles can settle to the bottom of the container where it can be shaken and/or agitated to resuspend or redisperse in the solution.

As used herein, "quetiapine" or "quetiapine fumarate" refers to the compound structurally shown below (as the free base):

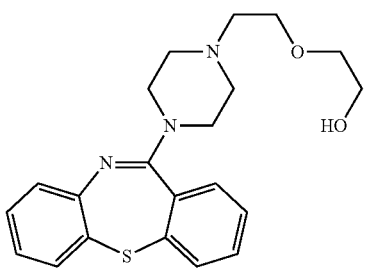 [SMILES: OCCOCCN1CCN(C2=Nc3ccccc3Sc3ccccc32)CC1]

and chemically designated as (free base): 2-(2-(4-Dibenzo[b,f][1,4]thiazepine-11-yl-1-piperazinyl)ethoxy)ethanol; having the formula $C_{21}H_{25}N_3O_2S$ and molar mass 383.5099 g/mol g mol$^{-1}$. Quetiapine can exist as the free base or as a pharmaceutically acceptable salt (e.g., quetiapine fumarate). When present in the oral liquid suspension described herein, the quetiapine free base or pharmaceutically acceptable salt thereof (e.g., quetiapine fumarate) functions as an active pharmaceutical ingredient.

The term "methylparaben" refers to the compound chemically designated as methyl 4-hydroxybenzoate, having the chemical formula $C_8H_8O_3$, and molar mas 152.149 g/mol. When present in the oral liquid suspension described herein, the methylparaben can function as a preservative.

The term "sodium benzoate" refers to the compound benzoate of soda, having the chemical formula $C_7H_5NaO_2$, and molar mass 144.105 g/mol. When present in the oral liquid suspension described herein, the sodium benzoate can function as a preservative. The sodium benzoate can be sodium benzoate powder.

The term "sorbitol" refers to the compound chemically designated as (2S,3R,4R,5R)-hexane-1,2,3,4,5,6-hexol, having the chemical formula $C_6H_{14}O_6$, and molar mass 182.17 g/mol. The sorbitol can be solid sorbitol. Alternatively, the sorbitol can be in solution (e.g., 70% solution of sorbitol). When present in the oral liquid suspension described herein, the sorbitol can function as a sweetening agent.

The term "saccharin" refers to the compound chemically designated as 1,1-dioxo-1,2-benzothiazol-3-one, having the chemical formula $C_7H_5NO_3S$, and molar mass 183.18 g/mol. When present in the oral liquid suspension described herein, the saccharin can function as a sweetening agent.

The saccharin can be saccharin sodium dihydrate powder. The term "saccharin sodium" refers to the sodium salt of saccharin. When present in the oral liquid suspension described herein, the saccharin sodium dihydrate powder can function as a sweetening agent.

The term "sucralose" refers to the compound chemically designated as 1,6-dichloro-1,6-dideoxy-β-D-fructofuranosyl-4-chloro-4-deoxy-α-D-galactopyranoside, having the chemical formula $C_{12}H_{19}Cl_3O_8$, and molar mass 397.64 g/mol. When present in the oral liquid suspension described herein, the sucralose can function as a sweetening agent.

The term "disodium phosphate" or "DSP" or "sodium hydrogen phosphate" or "sodium phosphate dibasic" refers to the inorganic compound with the formula $Na_2HPO_4$. and CAS Number 7558-79-4. The disodium phosphate can be sodium phosphate dibasic (dried). When present in the oral liquid suspension described herein, the disodium phosphate can function as a pH modifying agent.

As used herein, "microcrystalline cellulose" or "MCC" is a term for refined wood pulp. A naturally occurring polymer, it is composed of glucose units connected by a 1-4 beta glycosidic bond. These linear cellulose chains are bundled together as microfibril spiralled together in the walls of plant cell. When present in the oral liquid suspension described herein, the microcrystalline cellulose can function as a suspending agent, texturizer, anti-caking agent, or any combination thereof.

As used herein, "silicified microcrystalline cellulose" refers to MCC which is silicified. Silicification is the process in which organic matter becomes saturated with silica.

The term "PROSOLV@ SMCC" refers to the product silicified microcrystalline cellulose, which is a combination of microcrystalline cellulose (MCC) and colloidal silicon dioxide (CSD), sold under the trademark PROSOLV@ SMCC. The commercial product PROSOLV@ SMCC 50M has an average particle size determined by laser diffraction (μm) of 65. The commercial product PROSOLV@ SMCC 50M also has a bulk density (g/mL) of 0.25-0.37. PROSOLV@ SMCC is commercially available from JRS Pharma (Patterson, N.Y.), https://www.jrspharma.com/pharma_en/.

The term "propylene glycol" refers to the compound chemically designated as propane-1,2-diol, having the chemical formula $C_3H_8O_2$, and molar mass 76.095 g/mol. When present in the oral liquid suspension described herein, the propylene glycol can function as a preservative, solvent, viscosity-increasing agent, or any combination thereof.

The term "polyethylene glycol" or "PEG" refers to the compound chemically designated as poly(oxyethylene) or PEO (also referred to as poly(ethylene oxide) or PEO), having the chemical formula $C_{2n}H_{4n+2}O_{n+1}$, and molar mass 18.02+44.05n g/mol. PEG, PEO, and POE refer to an oligomer or polymer of ethylene oxide. The three names are chemically synonymous, but historically PEG is preferred in the biomedical field, whereas PEO is more prevalent in the field of polymer chemistry. Because different applications require different polymer chain lengths, PEG has tended to refer to oligomers and polymers with a molecular mass below 20,000 g/mol, PEO to polymers with a molecular mass above 20,000 g/mol, and POE to a polymer of any molecular mass. PEGs are typically prepared by polymerization of ethylene oxide and are commercially available over a wide range of molecular weights from 300 g/mol to 10,000,000 g/mol. When present in the oral liquid suspension described herein, the polyethylene glycol can function as a solvent, viscosity-increasing agent, suspending agent, or any combination thereof.

The polyethylene glycol can be polyethylene glycol 400. The term "polyethylene glycol 400" refers to a low-molecular-weight grade of polyethylene glycol, having the chemical formula $C_{2n}H_{4n+2}O_{n+1}$, wherein n=8.2 to 9.1, and molar mass 380-420 g/mol. When present in the oral liquid suspension described herein, the polyethylene glycol 400 can function as a solvent, viscosity-increasing agent, suspending agent, or any combination thereof.

The term "glycerin" or "glycerol" refers to the compound chemically designated as propane-1,2,3-triol, having the chemical formula $C_3H_8O_3$ and molar mass 92.094 g/mol. The glycerin can be glycerin, 99% natural. When present in the oral liquid suspension described herein, the glycerin can function as a preservative, sweetening agent, solvent, viscosity-increasing agent, or any combination thereof.

The term "xanthan gum" refers to a polysaccharide having the CAS Number 11138-66-2, and chemical formula $C_{35}H_{49}O_{29}$ (monomer). When present in the oral liquid suspension described herein, the xanthan gum can function as a viscosity-increasing agent, suspending agent, or a combination thereof.

The term "poloxamer 188" refers to the compound having the IUPAC name 2-(2-propoxypropoxy)ethanol; chemical formula $C_8H_{18}O_3$, CAS Number 9003-11-6, and molecular weight 162.23 g/mol. When present in the oral liquid suspension described herein, the poloxamer 188 can function as a surfactant, emulsifying agent, solubilizing agent, dispersing agent, or any combination thereof.

As used herein, "mental disorder" or "psychiatric disorder" refers to a behavioral or mental pattern that causes significant distress or impairment of personal functioning. Such features may be persistent, relapsing and remitting, or occur as a single episode. Many disorders have been described, with signs and symptoms that vary widely between specific disorders. Such disorders may be diagnosed by a mental health professional. The Diagnostic and Statistical Manual of Mental Disorders, Fifth Edition ("DSM-5") is the 2013 update to the Diagnostic and Statistical Manual of Mental Disorders, the taxonomic and diagnostic tool published by the American Psychiatric Association (APA). In the United States, the DSM serves as the principal authority for psychiatric diagnoses. Treatment recommendations are often determined by DSM classifications.

The mental disorder can include, e.g., any one or more of schizophrenia, bipolar I disorder manic episodes, bipolar disorder, depressive episodes. Specifically, the mental disorder can include, e.g., any one or more of schizophrenia in an adult, schizophrenia in an adolescent (13-17 years), bipolar mania in an adult, and bipolar mania in a children or adolescent (10-17 years).

As used herein, "bipolar disorder," previously known as manic depression, refers to a mental disorder that causes periods of depression and periods of abnormally elevated mood. The elevated mood is significant and is known as mania or hypomania, depending on its severity, or whether symptoms of psychosis are present. During mania, an individual behaves or feels abnormally energetic, happy, or irritable. Individuals often make poorly thought out decisions with little regard to the consequences. The need for sleep is usually reduced during manic phases. During periods of depression, there may be crying, a negative outlook on life, and poor eye contact with others.

As used herein, "schizophrenia" refers to a mental disorder characterized by continuous or relapsing episodes of psychosis. Major symptoms include hallucinations (typically hearing voices), delusions, and disorganized thinking. Other symptoms include social withdrawal, decreased emotional expression, and apathy.

As used herein, "combination therapy," "adjunctive therapy," or "polytherapy" refers to therapy that uses more than one medication or modality (versus "monotherapy," which is any therapy taken alone). Typically, these terms refer to using multiple therapies to treat a single disease, and often all the therapies are pharmaceutical (although it can also involve non-medical therapy, such as the combination of medications and talk therapy to treat depression). Monotherapy can be applied to any therapeutic approach, but it is most commonly used to describe the use of a single medication. Typically, monotherapy is selected because a single medication is adequate to treat the medical condition. However, monotherapies may also be used because of unwanted side effects or dangerous drug interactions.

As used herein, "CL/F" refers to the apparent total clearance of drug from plasma after oral administration. It is measured in units of volume/time (mL/min) or in units of volume/time/kg (mL/min/kg).

As used herein, "$T_{max}$" refers to time of maximum plasma concentration and is the time to reach maximum (peak) plasma concentration following drug administration. It is measured in units of time (hours).

As used herein, "$t_{1/2}$" refers to elimination half-life and is time to reach elimination half-life (to be used in one or non-compartmental model). It is measured in units of time (hours).

Specific Ranges, Values, Features, and Embodiments

The specific embodiments provided below describing the ranges, values, and features are for illustration purposes only, and do not otherwise limit the scope of the disclosed subject matter, as defined by the claims.

In specific embodiments, the oral liquid suspension includes quetiapine free base.

In specific embodiments, the oral liquid suspension includes quetiapine free base as the sole active pharmaceutical ingredient.

In specific embodiments, the oral liquid suspension includes a pharmaceutically acceptable salt of quetiapine.

In specific embodiments, the oral liquid suspension includes a pharmaceutically acceptable salt of quetiapine as the sole active pharmaceutical ingredient.

In specific embodiments, the oral liquid suspension includes quetiapine fumarate.

In specific embodiments, the oral liquid suspension includes quetiapine fumarate as the sole active pharmaceutical ingredient.

In specific embodiments, the oral liquid suspension includes quetiapine fumarate, present in an amount equal to 20 mg/ml quetiapine to 50 mg/ml quetiapine.

In specific embodiments, the oral liquid suspension includes quetiapine fumarate, present in an amount equal to 20 mg/ml quetiapine to 31.25 quetiapine.

In specific embodiments, the oral liquid suspension includes quetiapine fumarate, present in an amount equal to 25±5 mg/ml quetiapine.

In specific embodiments, the oral liquid suspension includes quetiapine fumarate, present in an amount equal to 25±2.5 mg/ml quetiapine.

In specific embodiments, the oral liquid suspension includes quetiapine fumarate, present in an amount equal to 25 mg/ml quetiapine.

In specific embodiments, the oral liquid suspension includes a one or more preservatives selected from ethanol, benzoic acid, benzyl alcohol, bronopol, butylated hydroxyanisole, butylparaben, calcium acetate, calcium chloride, calcium lactate, cetrimide, cetylpyridinium chloride, chlorhexidine, chlorobutanol, chlorocresol, chloroxylenol, citric acid monohydrate, ethylparaben, glycerin, hexetidine, imidurea, isopropyl alcohol, lactic acid, methylparaben, monothioglycerol, parabens, pentetic acid, phenoxyethanol, phenylethyl alcohol, potassium benzoate, potassium metabisulfite, potassium sorbate, propionic acid, propyl gallate, propylene glycol, propylparaben, propylparaben sodium, sodium acetate, sodium benzoate, sodium borate, sodium lactate, sodium metabisulfite, sodium propionate, sodium sulfite, sorbic acid, sulfobutyl ether β-cyclodextrin, edetic acid, thimerosal, xanthan, and combinations thereof.

In specific embodiments, the oral liquid suspension includes one or more sweeteners selected from acesulfame potassium, alitame, aspartame, dextrose, erythritol, fructose, glycerin, isomalt, lactitol, glucose, maltitol, maltose, mannitol, monk fruit extract, neohesperidin dihydrochalcone, neotame, saccharin, saccharin sodium, sodium cyclamate, sorbitol, stevia, sucralose, sucrose, tagatose, thaumatin, trehalose, xylitol, and combinations thereof.

In specific embodiments, the oral liquid suspension includes one or more solvents selected from albumin, ethanol, almond oil, benzyl alcohol, benzyl benzoate, butylene glycol, castor oil, corn oil (maize), cottonseed oil, dimethyl ether, dimethylacetamide, ethyl lactate, ethyl oleate, glycerin, isopropyl alcohol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl castor oil, propylene carbonate, propylene glycol, pyrrolidone, safflower oil, sesame oil, soybean oil, sunflower oil, triacetin, tricaprylin, triethanolamine, triethyl citrate, triolein, water, and combinations thereof.

In specific embodiments, the oral liquid suspension includes one or more surfactants selected from detergents, wetting agents, emulsifiers, foaming agents, dispersants, and combinations thereof.

In specific embodiments, the oral liquid suspension includes one or more anticaking agents selected from tribasic calcium phosphate, calcium silicate, colloidal silicon dioxide, hydrophobic colloidal silica, magnesium oxide, magnesium silicate, magnesium trisilicate, talc, and combinations thereof.

In specific embodiments, the oral liquid suspension includes one or more viscosity-increasing agents selected from acacia, agar, alginic acid, bentonite, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, guar gum, hectorite, hydrogenated vegetable oil type I, hydrophobic colloidal silica, hydroxyethyl cellulose, hydroxyethylmethyl cellulose, hydroxypropyl cellulose, hydroxypropyl starch, hypromellose, magnesium aluminum silicate, maltodextrin, methylcellulose, myristyl alcohol, polydextrose, polyethylene glycol, polyvinyl alcohol, potassium chloride, povidone, propylene glycol alginate, saponite, sodium alginate, sodium chloride, starch, stearyl alcohol, sucrose, sulfobutyl ether β-cyclodextrin, tragacanth, xanthan gum, and combinations thereof.

In specific embodiments, the oral liquid suspension includes one or more suspending agents selected from acacia, agar, alginic acid, bentonite, calcium stearate, carbomers, carboxymethylcellulose calcium, carboxymethylcellulose sodium, carrageenan, powdered cellulose, cellulose, microcrystalline cellulose, carboxymethylcellulose sodium, ceratonia, colloidal silicon dioxide, dextrin, gelatin, guar gum, hectorite, hydrophobic colloidal silica, hydroxyethyl cellulose, hydroxyethylmethyl cellulose, hydroxypropyl cellulose, hypromellose, kaolin, magnesium aluminum silicate, maltitol solution, medium-chain triglycerides, methylcellulose, silicified microcrystalline cellulose, phospholipids, polycarbophil, polyethylene glycol, polyoxyethylene sorbitan fatty acid esters, potassium alginate, povidone, propylene glycol alginate, saponite, sesame oil, sodium alginate, sodium starch glycolate, sorbitan esters, sucrose, tragacanth, vitamin E polyethylene glycol succinate, and xanthan gum, the product microcrystalline cellulose (MCC) and colloidal silicon dioxide (CSD) sold under the trademark PROSOLV® SMCC 50M, and combinations thereof.

In specific embodiments, the oral liquid suspension includes one or more acidifying agents selected from sodium phosphate dibasic, adipic acid, ammonium chloride, citric acid monohydrate, diluted hydrochloric acid, lactic acid, propionic acid, tartaric acid, and combinations thereof.

In specific embodiments, the oral liquid suspension includes one or more flavoring agents selected from cherry flavor, grape, peppermint, and combinations thereof.

In specific embodiments, the oral liquid suspension includes methylparaben.

In specific embodiments, the oral liquid suspension includes methylparaben, present in 1±0.2 mg/ml.

In specific embodiments, the oral liquid suspension includes methylparaben, present in 1 mg/ml.

In specific embodiments, the oral liquid suspension includes sodium benzoate powder.

In specific embodiments, the oral liquid suspension includes sodium benzoate powder, present in 0.3±0.06 mg/ml.

In specific embodiments, the oral liquid suspension includes sodium benzoate powder, present in 0.3 mg/ml.

In specific embodiments, the oral liquid suspension includes saccharin sodium dihydrate powder.

In specific embodiments, the oral liquid suspension includes saccharin sodium dihydrate powder, present in 0.8±0.04 mg/ml.

In specific embodiments, the oral liquid suspension includes saccharin sodium dihydrate powder, present in 0.8 mg/ml.

In specific embodiments, the oral liquid suspension includes sodium phosphate dibasic.

In specific embodiments, the oral liquid suspension includes sodium phosphate dibasic, present in 0.3±0.06 mg/ml.

In specific embodiments, the oral liquid suspension includes sodium phosphate dibasic, present in 0.3 mg/ml.

In specific embodiments, the oral liquid suspension includes sorbitol solution 70%.

In specific embodiments, the oral liquid suspension includes sorbitol solution 70%, present in 30±6 mg/ml.

In specific embodiments, the oral liquid suspension includes sorbitol solution 70%, present in 30 mg/ml.

In specific embodiments, the oral liquid suspension includes propylene glycol.

In specific embodiments, the oral liquid suspension includes propylene glycol, present in 22.5±5 mg/ml.

In specific embodiments, the oral liquid suspension includes propylene glycol, present in 22.5 mg/ml.

In specific embodiments, the oral liquid suspension includes glycerin 99.7% natural grade.

In specific embodiments, the oral liquid suspension includes glycerin 99.7% natural grade, present in 50±10 mg/ml.

In specific embodiments, the oral liquid suspension includes glycerin 99.7% natural grade, present in 50 mg/ml.

In specific embodiments, the oral liquid suspension includes the product microcrystalline cellulose (MCC) and colloidal silicon dioxide (CSD) sold under the trademark PROSOLV® SMCC 50.

In specific embodiments, the oral liquid suspension includes the product microcrystalline cellulose (MCC) and colloidal silicon dioxide (CSD) sold under the trademark PROSOLV@SMCC 50, present in 12.6±3 mg/ml.

In specific embodiments, the oral liquid suspension includes the product microcrystalline cellulose (MCC) and colloidal silicon dioxide (CSD) sold under the trademark PROSOLV@SMCC 50, present in 12.6 mg/ml.

In specific embodiments, the oral liquid suspension includes carboxymethylcellulose sodium, medium viscosity (2% aqueous solution at 25° C. is 400 cps to 800 cps).

In specific embodiments, the oral liquid suspension includes carboxymethylcellulose sodium, medium viscosity (2% aqueous solution at 25° C. is 400 cps to 800 cps), present in 1.8±0.4 mg/ml.

In specific embodiments, the oral liquid suspension includes carboxymethylcellulose sodium, medium viscosity (2% aqueous solution at 25° C. is 400 cps to 800 cps), present in 1.8 mg/ml.

In specific embodiments, the oral liquid suspension includes xanthan gum.

In specific embodiments, the oral liquid suspension includes xanthan gum, present in 1.8±0.4 mg/ml.

In specific embodiments, the oral liquid suspension includes xanthan gum, present in 1.8 mg/ml.

In specific embodiments, the oral liquid suspension includes purified water.

In specific embodiments, the oral liquid suspension includes purified water, present in 787.046±150 mg/ml.

In specific embodiments, the oral liquid suspension includes purified water, present in 787.046 mg/ml.

In specific embodiments, the oral liquid suspension includes poloxamer 188 (2-(2-propoxypropoxy)ethanol).

In specific embodiments, the oral liquid suspension includes poloxamer 188 (2-(2-propoxypropoxy)ethanol), present in 6±1.2 mg/ml.

In specific embodiments, the oral liquid suspension includes poloxamer 188 (2-(2-propoxypropoxy)ethanol), present in 6 mg/ml.

In specific embodiments, the oral liquid suspension includes polyethylene glycol 400.

In specific embodiments, the oral liquid suspension includes polyethylene glycol 400, present in 50±10 mg/ml.

In specific embodiments, the oral liquid suspension includes polyethylene glycol 400, present in 50 mg/ml.

In specific embodiments, the oral liquid suspension includes sucralose.

In specific embodiments, the oral liquid suspension includes sucralose, present in 5±1 mg/ml.

In specific embodiments, the oral liquid suspension includes sucralose, present in 5 mg/ml.

In specific embodiments, the oral liquid suspension further includes one or more flavoring agents.

In specific embodiments, the oral liquid suspension further includes cherry flavor (natural and artificial).

In specific embodiments, the oral liquid suspension further includes cherry flavor (natural and artificial), present in 2.00±0.04 mg/ml.

In specific embodiments, the oral liquid suspension further includes cherry flavor (natural and artificial), present in 2.00 mg/ml.

In specific embodiments, the oral liquid suspension further includes one or more colorants.

In specific embodiments, the oral liquid suspension further includes FD&C red #40 and FD&C yellow #6.

In specific embodiments, the oral liquid suspension further includes FD&C red #40, present in 0.02±0.004 mg/ml and FD&C yellow #6, present in 0.002±0.0004 mg/ml.

In specific embodiments, the oral liquid suspension further includes FD&C red #40, present in 0.02 mg/ml and FD&C yellow #6, present in 0.002 mg/ml.

In specific embodiments, the oral liquid suspension includes:

| % W/V | Material/Component |
|---|---|
| 28.83 mg/ml | quetiapine fumarate |
| 1 mg/ml | methylparaben |
| 0.3 mg/ml | sodium benzoate powder |
| 0.8 mg/ml | saccharin sodium dihydrate powder |
| 0.3 mg/ml | sodium phosphate dibasic |
| 30 mg/ml | sorbitol solution 70% |
| 22.5 mg/ml | propylene glycol |
| 50 mg/ml | glycerin 99.7% natural grade |
| 12.6 mg/ml | PROSOLV® SMCC 50 (silicified microcrystalline cellulose) |
| 1.8 mg/ml | carboxymethylcellulose sodium, medium viscosity (2% aqueous solution at 25° C. is 400-800 cps) |
| 1.8 mg/ml | xanthan gum |
| 787.046 mg/ml | purified water |
| 6 mg/ml | Poloxamer 188 (2-(2-propoxypropoxy)ethanol) |
| 50 mg/ml | polyethylene glycol 400 |
| 5 mg/ml | sucralose |
| 2.00 mg/ml | cherry flavor (natural and artificial) |
| 0.02 mg/ml | FD&C red #40 |
| 0.002 mg/ml | FD&C yellow #6 |
| TOTAL 998.198 mg/ml | |

In specific embodiments, the oral liquid suspension is manufactured from the drug substance quetiapine fumarate having the following particle size distribution. $D_{90}$ of not more than 60±12 microns.

In specific embodiments, the oral liquid suspension is manufactured from the drug substance quetiapine fumarate having the following particle size distribution: $D_{90}$ of not more than 60 microns.

In specific embodiments, the drug product oral liquid suspension has the following particle size distribution: $D_{90}$ of not more than 300±60 microns.

In specific embodiments, the drug product oral liquid suspension has the following particle size distribution: $D_{90}$ of not more than 300 microns.

In specific embodiments, the drug product oral liquid suspension has the following particle size distribution: $D_{90}$ of not more than 100±20 microns.

In specific embodiments, the drug product oral liquid suspension has the following particle size distribution: $D_{50}$ of not more than 100 microns.

In specific embodiments, the drug product oral liquid suspension has the following particle size distribution: $D_{10}$ of not more than 30±6 microns.

In specific embodiments, the drug product oral liquid suspension has the following particle size distribution: $D_{10}$ of not more than 30 microns.

In specific embodiments, the drug product oral liquid suspension has the following particle size distribution: $D_{90}$ of not more than 300±60 microns, $D_{50}$ of not more than 100±20 microns, and $D_{10}$ of not more than 30±6 microns.

In specific embodiments, the drug product oral liquid suspension has the following particle size distribution: $D_{90}$ of not more than 300 microns, $D_{50}$ of not more than 100 microns, and $D_{10}$ of not more than 30 microns.

In specific embodiments, the oral liquid suspension has a viscosity at 25° C. of 10 millipoises to 50 millipoises.

In specific embodiments, the oral liquid suspension has a viscosity at 25° C. of 15 millipoises to 40 millipoises.

In specific embodiments, the oral liquid suspension has a viscosity at 25° C. of 20 millipoises to 35 millipoises.

In specific embodiments, the oral liquid suspension has a pH of 5-6.5.

In specific embodiments, the oral liquid suspension has a pH of 5.25-6.25.

In specific embodiments, the oral liquid suspension has a specific gravity of not more than 1.2.

In specific embodiments, the oral liquid suspension, while packaged in a container, is essentially free from microbial growth for at least 24 months under ambient conditions.

In specific embodiments, the oral liquid suspension, while packaged in a container, is essentially free from microbial growth for at least 36 months under ambient conditions.

In specific embodiments, the oral liquid suspension, while packaged in a container, is essentially free from *Escherichia coli* (*E. coli*) for at least 24 months under ambient conditions.

In specific embodiments, the oral liquid suspension, while packaged in a container, is essentially free from *Escherichia coli* (*E. coli*) for at least 36 months under ambient conditions.

In specific embodiments, the oral liquid suspension, while packaged in a container, is essentially free from *Burkholderia cepacian* complex for at least 24 months under ambient conditions.

In specific embodiments, the oral liquid suspension, while packaged in a container, is essentially free from *Burkholderia cepacian* complex for at least 36 months under ambient conditions.

In specific embodiments, the oral liquid suspension is an immediate release (IR) dosage form.

In specific embodiments, the oral liquid suspension is an immediate release dosage form that exhibits in-vitro dissolution rate more than 80% of drug release within 20 minutes, when said dosage form is placed in a dissolution vessel filled with 900 ml of deionized water maintained at 37±0.5° C. and stirred at a paddle speed of 50 rpm using a USP Type II (paddle) apparatus.

In specific embodiments, the oral liquid suspension is indicated for at least one of: (i) Schizophrenia Adults, (ii) Schizophrenia Adolescents (13-17 years), (iii) Bipolar Mania Adults Monotherapy or as an adjunct to lithium or divalproex, (iv) Bipolar Mania Children and Adolescents (10-17 years), Monotherapy, and (v) Bipolar Depression Adults.

In specific embodiments, the oral liquid suspension is indicated for at least one of: (i) Schizophrenia Adults, (ii) Schizophrenia Adolescents (13-17 years), (iii) Bipolar Mania Adults Monotherapy or as an adjunct to lithium or divalproex, (iv) Bipolar Mania Children and Adolescents (10-17 years), Monotherapy, and (v) Bipolar Depression Adults; wherein the oral liquid suspension further has the following dosage and administration of quetiapine fumarate:

In specific embodiments, the oral liquid suspension is indicated for a mental disorder.

In specific embodiments, the mental disorder includes at least one of Schizophrenia, Bipolar I disorder manic episodes, and Bipolar disorder depressive episodes.

In specific embodiments, the mental disorder includes major depressive disorder, with adjunctive antidepressant.

In specific embodiments, 0.1 ml to 50.0 ml of the oral liquid suspension is orally administered to the subject.

In specific embodiments, 1 ml to 2.5 ml of the oral liquid suspension is orally administered to the subject.

In specific embodiments, an amount of the oral liquid suspension is orally administered to the subject, sufficient to orally deliver to the subject 25 mg to 400 mg of quetiapine fumarate.

In specific embodiments, an amount of the oral liquid suspension is orally administered to the subject, sufficient to orally deliver to the subject 25 mg, 50 mg, 100 mg, 200 mg, 300 mg, or 400 mg of quetiapine fumarate.

In specific embodiments, an amount of the oral liquid suspension is orally administered to the subject, sufficient to orally deliver to the subject a maximum dose of up to 800 mg/day of quetiapine fumarate.

In specific embodiments, an amount of the oral liquid suspension is orally administered to the subject, sufficient to orally deliver to the subject a maximum dose of 300 mg/day to 800 mg/day quetiapine fumarate.

In specific embodiments, an amount of the oral liquid suspension is orally administered to the subject, sufficient to orally deliver to the subject a maximum dose of 300 mg/day, 600 mg/day, 750 mg/day, or 800 mg/day of quetiapine fumarate.

In specific embodiments, an amount of the oral liquid suspension is orally administered to the subject, sufficient to orally deliver to the subject an initial dose of 25 mg twice daily of quetiapine fumarate.

In specific embodiments, an amount of the oral liquid suspension is orally administered to the subject, sufficient to orally deliver to the subject an initial dose of 50 mg twice daily of quetiapine fumarate.

In specific embodiments, an amount of the oral liquid suspension is orally administered to the subject, sufficient to orally deliver to the subject an initial dose of 50 mg once daily at bedtime of quetiapine fumarate.

In specific embodiments, an amount of the oral liquid suspension is orally administered to the subject, sufficient to orally deliver to the subject 150 mg/day of quetiapine fumarate to 750 mg/day of quetiapine fumarate.

| Indication | Initial Dose (Quetiapine Fumarate) | Recommended Dose (Quetiapine Fumarate) | Maximum Dose (Quetiapine Fumarate) |
| --- | --- | --- | --- |
| Schizophrenia Adults | 25 mg twice daily | 150-750 mg/day | 750 mg/day |
| Schizophrenia Adolescents (13-17 years) | 25 mg twice daily | 400-800 mg/day | 800 mg/day |
| Bipolar Mania Adults Monotherapy or as an adjunct to lithium or divalproex | 50 mg twice daily | 400-800 mg/day | 800 mg/day |
| Bipolar Mania Children and Adolescents (10-17 years), Monotherapy | 25 mg twice daily | 400-600 mg/day | 600 mg/day |
| Bipolar Depression Adults | 50 mg once daily at bedtime | 300 mg/day | 300 mg/day |

In specific embodiments, an amount of the oral liquid suspension is orally administered to the subject, sufficient to orally deliver to the subject 300 mg/day of quetiapine fumarate.

In specific embodiments, an amount of the oral liquid suspension is orally administered to the subject, sufficient to orally deliver to the subject 400 mg/day of quetiapine fumarate to 600 mg/day of quetiapine fumarate.

In specific embodiments, an amount of the oral liquid suspension is orally administered to the subject, sufficient to orally deliver to the subject 400 mg/day of quetiapine fumarate to 800 mg/day of quetiapine fumarate.

In specific embodiments, the peak plasma concentrations is reached in less than 1.5 hours.

In specific embodiments, the peak plasma concentrations is reached in less than 1.25 hours.

In specific embodiments, relative to oral tablets containing an equivalent amount of quetiapine fumarate, administration of the oral liquid suspension results in a lower incidence, severity, and/or duration of adverse reactions including at least one of hyperglycemia, dyslipidemia, somnolence, dry mouth, dizziness, constipation, asthenia, abdominal pain, postural hypotension, pharyngitis, weight gain, lethargy, ALT increased, dyspepsia, fatigue, increased appetite, nausea, vomiting, and tachycardia.

In specific embodiments, upon administration under fasted conditions of a healthy adult subject with a mental disorder taking no other medications, the oral liquid suspension exhibits a single-dose administration pharmacokinetic profile including: AUC, 0→24 (micrograms per ml) of 308±60.

In specific embodiments, upon administration under fasted conditions of a healthy adult subject with a mental disorder taking no other medications, the oral liquid suspension exhibits a single-dose administration pharmacokinetic profile including: $C_{max}$ (micrograms per ml) of 80-120.

In specific embodiments, upon administration under fasted conditions of a healthy adult subject with a mental disorder taking no other medications, the oral liquid suspension exhibits a single-dose administration pharmacokinetic profile including: $T_{max}$(h) of 1-2.

In specific embodiments, upon administration under fasted conditions of a healthy adult subject with a mental disorder taking no other medications, the oral liquid suspension exhibits a single-dose administration pharmacokinetic profile including: $t_{1/2}$(h) of 7.0 (single dose).

In specific embodiments, upon administration under fasted conditions of a healthy adult subject with a mental disorder taking no other medications, the oral liquid suspension exhibits a single-dose administration pharmacokinetic profile including: AUC, 0-24 (micrograms per ml) of 308±60; $C_{max}$ (micrograms per ml) of 80-120; $T_{max}$(h) of 1-2; and $t_{1/2}$(h) of 7.0 (single dose).

In specific embodiments, prior to administration, the oral liquid suspension is shaken.

In specific embodiments, prior to administration, the oral liquid suspension is shaken, to sufficiently re-disperse the ingredients therein, such that uniform dosing is achieved.

In specific embodiments, prior to administration, the oral liquid suspension is shaken for up to 60 seconds.

In specific embodiments, prior to administration, the oral liquid suspension is shaken for 30 to 60 seconds.

ENUMERATED EMBODIMENTS

Specific enumerated embodiments <1> to <26> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<Embodiment 1> An oral liquid suspension comprising:
quetiapine fumarate, present in an amount equal to 25 mg/ml quetiapine;
methylparaben, present in 1 mg/ml;
sodium benzoate powder, present in 0.3 mg/ml;
saccharin sodium dihydrate powder, present in 0.8 mg/ml;
sodium phosphate dibasic, present in 0.3 mg/ml;
sorbitol solution 70%, present in 30 mg/ml,
propylene glycol, present in 22.5 mg/ml;
glycerin 99.7% natural grade, present in 50 mg/ml;
the product microcrystalline cellulose (MCC) and colloidal silicon dioxide (CSD) sold under the trademark PROSOLV® SMCC 50, present in 12.6 mg/ml;
carboxymethylcellulose sodium, medium viscosity (2% aqueous solution at 25° C. is 400 cps to 800 cps), present in 1.8 mg/ml;
xanthan gum, present in 1.8 mg/ml;
purified water, present in 787.046 mg/ml;
poloxamer 188 (2-(2-propoxypropoxy)ethanol), present in 6 mg/ml;
polyethylene glycol 400, present in 50 mg/ml; and
sucralose, present in 5 mg/ml.

<Embodiment 2> The oral liquid suspension of the embodiment, wherein the oral liquid suspension is manufactured from the drug substance quetiapine fumarate having the following particle size distribution: Do of not more than 60 microns.

<Embodiment 3> The oral liquid suspension of any one of the above embodiments, wherein the drug product oral liquid suspension has the following particle size distribution: $D_{90}$ of not more than 300 microns, $D_{50}$ of not more than 100 microns, and $D_{10}$ of not more than 30 microns.

<Embodiment 4> The oral liquid suspension of any one of the above embodiments, having a viscosity at 25° C. of 15 millipoises to 40 millipoises.

<Embodiment 5> The oral liquid suspension of any one of the above embodiments, having a pH of 5-6.5.

<Embodiment 6> The oral liquid suspension of any one of the above embodiments, having a specific gravity of not more than 1.2.

<Embodiment 7> The oral liquid suspension of any one of the above embodiments, while packaged in a container, is essentially free from microbial growth for at least 24 months under ambient conditions.

<Embodiment 8> The oral liquid suspension of any one of the above embodiments, while packaged in a container, is essentially free from *Escherichia coli* (*E. coli*) for at least 24 months under ambient conditions.

<Embodiment 9> The oral liquid suspension of any one of the above embodiments, while packaged in a container, is essentially free from *Burkholderia cepacia* complex for at least 24 months under ambient conditions.

<Embodiment 10> The oral liquid suspension of anyone of the above embodiments, which is an immediate release dosage form.

<Embodiment 11> The oral liquid suspension of any one of the above embodiments, which is an immediate release dosage form that exhibits in-vitro dissolution rate more than 80% of drug release within 20 minutes, when said dosage form is placed in a dissolution vessel filled with 900 ml of deionized water maintained at 37±0.5° C. and stirred at a paddle speed of 50 rpm using a USP Type I (paddle) apparatus.

<Embodiment 12> The oral liquid suspension of any one of the above embodiments, further comprising one or more flavoring agents.

<Embodiment 13> The oral liquid suspension of any one of the above embodiments, further comprising cherry flavor (natural and artificial), present in 2.00 mg/ml.

<Embodiment 14> The oral liquid suspension of any one of the above embodiments, further comprising one or more colorants.

<Embodiment 15> The oral liquid suspension of any one of the above embodiments, further comprising FD&C red #40, present in 0.02 mg/ml and FD&C yellow #6, present in 0.002 mg/ml.

<Embodiment 16> The oral liquid suspension of any one of the above embodiments, comprising:

| % W/V | Material/Component |
|---|---|
| 28.83 mg/ml | quetiapine fumarate |
| 1 mg/ml | methylparaben |
| 0.3 mg/ml | sodium benzoate powder |
| 0.8 mg/ml | saccharin sodium dihydrate powder |
| 0.3 mg/ml | sodium phosphate dibasic |
| 30 mg/ml | sorbitol solution 70% |
| 22.5 mg/ml | propylene glycol |
| 50 mg/ml | glycerin 99.7% natural grade |
| 12.6 mg/ml | PROSOLV® SMCC 50 (silicified microcrystalline cellulose) |
| 1.8 mg/ml | carboxymethylcellulose sodium, medium viscosity (2% aqueous solution at 25° C. is 400-800 cps) |
| 1.8 mg/ml | xanthan gum |
| 787.046 mg/ml | purified water |
| 6 mg/ml | Poloxamer 188 (2-(2-propoxypropoxy)ethanol) |
| 50 mg/ml | polyethylene glycol 400 |
| 5 mg/ml | sucralose |
| 2.00 mg/ml | cherry flavor (natural and artificial) |
| 0.02 mg/ml | FD&C red #40 |
| 0.002 mg/ml | FD&C yellow #6 |
| TOTAL 998.198 mg/ml | |

<Embodiment 17> A method for treating a mental disorder in a subject, the method comprising administering to a subject suffering from the disorder an effective amount of the oral liquid suspension of any one of the above embodiments.

<Embodiment 18> The method of embodiment <17>, wherein the mental disorder comprises at least one of Schizophrenia, Bipolar I disorder manic episodes, and Bipolar disorder depressive episodes.

<Embodiment 19> The method of anyone of embodiments <17> to <18>, wherein the effective amount is 0.1 ml to 50.0 ml.

<Embodiment 20> The method of anyone of embodiments <17> to <19>, wherein the effective amount is sufficient to orally deliver 25 mg to 400 mg of quetiapine fumarate.

<Embodiment 21> The method of anyone of embodiments <17> to <20>, wherein the effective amount is sufficient to orally deliver to the subject 25 mg, 50 mg, 100 mg, 200 mg, 300 mg, or 400 mg of quetiapine fumarate.

<Embodiment 22> The method of any one of embodiments <17> to <21>, wherein the peak plasma concentrations is reached in less than 1.5 hours.

<Embodiment 23> The method of any one of embodiments <17> to <22>, wherein the oral liquid suspension is indicated for at least one of: (i) Schizophrenia Adults, (ii) Schizophrenia Adolescents (13-17 years), (iii) Bipolar Mania Adults Monotherapy or as an adjunct to lithium or divalproex, (iv) Bipolar Mania Children and Adolescents (10-17 years), Monotherapy, and (v) Bipolar Depression Adults;

the oral liquid suspension further having the following dosage and administration of quetiapine fumarate:

| Indication | Initial Dose (Quetiapine Fumarate) | Recommended Dose (Quetiapine Fumarate) | Maximum Dose (Quetiapine Fumarate) |
|---|---|---|---|
| Schizophrenia Adults | 25 mg twice daily | 150-750 mg/day | 750 mg/day |
| Schizophrenia Adolescents (13-17 years) | 25 mg twice daily | 400-800 mg/day | 800 mg/day |
| Bipolar Mania Adults Monotherapy or as an adjunct to lithium or divalproex | 50 mg twice daily | 400-800 mg/day | 800 mg/day |
| Bipolar Mania Children and Adolescents (10-17 years), Monotherapy | 25 mg twice daily | 400-600 mg/day | 600 mg/day |
| Bipolar Depression Adults | 50 mg once daily at bedtime | 300 mg/day | 300 mg/day |

<Embodiment 24> The method of anyone of embodiments <17> to <23>, wherein relative to oral tablets containing an equivalent amount of quetiapine fumarate, administration of the oral liquid suspension results in a lower incidence, severity, and/or duration of adverse reactions including at least one of hyperglycemia, dyslipidemia, somnolence, dry mouth, dizziness, constipation, asthenia, abdominal pain, postural hypotension, pharyngitis, weight gain, lethargy, ALT increased, dyspepsia, fatigue, increased appetite, nausea, vomiting, and tachycardia.

<Embodiment 25> The method of anyone of embodiments <17> to <24>, wherein upon administration under fasted conditions of a healthy adult subject with a mental disorder taking no other medications, the oral liquid suspension exhibits a single-dose administration pharmacokinetic profile including:

AUC, 0→24 (micrograms per ml) of 308±60;
a $C_{max}$ (micrograms per ml) of 80-120;
$T_{max}$(h) of 1-2; and
$t_{1/2}$(h) of 7.0 (single dose).

<Embodiment 26> The method of anyone of embodiments <17> to <25>, wherein prior to administration, the oral liquid suspension is shaken, to sufficiently re-disperse the ingredients therein, such that uniform dosing is achieved.

The following examples are intended for illustration only and are not intended to limit the scope of the invention in any way.

EXAMPLES

Example 1-Formulation

An oral liquid suspension containing quetiapine fumarate was formulated from the following substances in the amounts specified.

| % W/V (mg/ml) | Material/Component |
|---|---|
| 28.83 | quetiapine fumarate |
| 1 | methylparaben |
| 0.3 | sodium benzoate powder |
| 0.8 | saccharin sodium dihydrate powder |
| 0.3 | sodium phosphate dibasic |
| 30 | sorbitol solution 70% |
| 22.5 | propylene glycol |
| 50 | glycerin 99.7% natural grade |
| 12.6 | PROSOLV ® SMCC 50 (silicified microcrystalline cellulose) |
| 1.8 | carboxymethylcellulose sodium, medium viscosity (2% aqueous solution at 25° C. is 400-800 cps) |
| 1.8 | xanthan gum |
| 787.046 | purified water |
| 6 | Poloxamer 188 (2-(2-propoxypropoxy)ethanol) |
| 50 | polyethylene glycol 400 |
| 5 | sucralose |
| 2.00 | cherry flavor (natural and artificial) |
| 0.02 | FD&C red #40 |
| 0.002 | FD&C yellow #6 |
| TOTAL 998.198 | |

Example 2-Method of Manufacturing

The oral liquid suspension containing quetiapine fumarate of Example 1 was manufactured as follows.

Phase 1 Preparation:
1. Mix propylene glycol and methylparaben until completely dissolved and homogeneous.

Phase 2 Preparation:
1. Mix water, sodium carboxymethyl cellulose, xanthan gum, and the product microcrystalline cellulose (MCC) and colloidal silicon dioxide (CSD) sold under the trademark PROSOLV® SMCC 50M until completely dissolved and homogeneous.
2. Add sodium benzoate, sodium phosphate dibasic, and sodium saccharin and mix until completely dissolved and homogeneous.
3. Add poloxamer and polyethylene glycol; and mix until completely dissolved and homogeneous.
4. Add sorbitol, 70% solution and mix until completely dissolved and homogeneous.
5. Add quetiapine fumarate and mix until completely dissolved and homogeneous.

Phase 3 Preparation:
1. Add Phase 1 into Phase 2 with continuous mixing, until completely dissolved and homogeneous.
2. Add glycerin and mix until completely dissolved and homogeneous.
3. Add FD&C Red #40, FD&C Yellow #6, cherry flavor, and sucralose; and mix until completely dissolved and homogeneous.
4. Semi-automatic fill in packaging (bottle) and manual labeling.
5. Optionally check appearance, pH, viscosity, particle size distribution, assay, dosage uniformity, sedimentation rate, dissolution, deliverable volume, and/or micro testing.

Example 3—Packaging

The oral liquid suspension of Example 1 was manufactured for packaging, shipment, storage, and for use with the following.

| Container | Oral Dispenser |
|---|---|
| Plastic bottle | Measuring cup |
| Glass bottle | Measuring syringe |
| | Measuring dropper |

Example 4—Method of Administration

The oral liquid suspension of Example 1 was formulated for administration that includes the following.

1. Shake well before using to ensure sufficient redispersion and content uniformity.
2. Measure the prescribed dose of the oral liquid suspension into the dispenser.
3. Orally administer the dose from the dispenser to the subject (with or without food). The medication may be administered by the patient, a caregiver, or a health professional.

Example 5—Test Methods

1.1 Sedimentation Rate
Equipment

| ITEM | EQUIPMENT | MANUFACTURER/MODEL* | ASSET # |
|---|---|---|---|
| 1 | Digital Timer | VWR | PTS 291 |
| 2 | 100-mL graduated cylinders, Class A Glass | N/A | N/A |
| 3 | Digital Camera (with time-stamp) | N/A | PTS |

*Or similar calibrated/qualified equipment

Procedure
1. Shake the suspension well as described.
2. Pour 50 mL of the sample into a 100-mL measuring cylinder and start the timer.
3. Securely seal the measuring cylinder with parafilm to prevent water loss.
4. Measure and record the amount of sediment after 10 minutes, 2 hours and 24 hours. Capture images clearly showing the graduations and sample ID at each timepoint.

Tolerance

Not more than (NMT) 2.5 mL after 24 hrs (from a 50-mL volume).

1.2 Assessment of Re-Dispersibility
Procedure
1. Perform the procedure described in section 3.10: SEDIMENTITON RATE.
2. After 24 hours, invert the measuring cylinder through 180°
3. Return to the upright position using a splashing motion to dislodge any sediment.
4. Repeat the inversions until the suspension is uniformly distributed. Record the number of inversions required to restore uniformity.

Calculation
1. If uniformity is attained in one inversion, the suspension has 100% ease of re-dispersibility.
2. Every additional inversion decreases the ease of re-dispersibility by 5%.

Viscosity Measurements:

1.3 Rheological Consideration of a Suspension is of Great Importance for the Stability Because Viscosity can Modify the Sedimentation Rates. Maintaining the Proper Viscosity of Suspensions is Also Important to Ensure the Accuracy of Dosing and Ease of Application.

Viscosity (Usp <912>)
Equipment

| ITEM | EQUIPMENT | MANUFACTURER/MODEL* | ASSET # |
|---|---|---|---|
| 1 | Rotary Viscometer | US Solid/USS DVT6 | PTS 096 |
| 2 | Spindle | US Solid/#2 size | N/A |
| 3 | Digital Thermometer | Di stek/4600 | PTS 131 |
| 4 | Beakers, Class A Glass | N/A | N/A |

*Or similar calibrated/qualified equipment

Standards

| ITEM | REAGENT DESCRIPTION | VENDOR/CATALOG NUMBER** |
|---|---|---|
| 1 | Cannon Viscosity Standards 1.2 mm$^2$/s | Fisher Chemical/22-288-554 |

**Or equivalent

Test Conditions

| | |
|---|---|
| Temperature: | 22-25° C. |
| Mode: | mPa · s |
| Spindle: | #1 |
| Spindle speed: | 60 rpm |

Procedure
1. Check the calibration between 22-25° C. using the viscosity standard. The viscosity values of the calibration standards should bracket the expected viscosity value of the sample liquid. The measured apparent viscosity is +5% of the stated value.
2. Allow all test samples to stabilize between 22-25° C.
3. Fill a glass beaker so that the spindle is immersed to the recommended depth maintaining at least 1 cm clearance from the bottom and side of the container.
4. Report the size and geometry of spindle the rotational speed of the spindle
5. SET spindle #1 and 60 RPM. Ensure that the instrument is level and record the sample temperature when the display is stable. Press OK and record the viscosity when the instrument completes the measurement cycle and Press RESET.
6. Repeat step 5 to perform the triplicate measurements.

Tolerance 15-40 mPa.

The pascal (Pa) is the unit of pressure or stress in the International System of Units (SI). A centipoise (cP) is a non-SI measurement unit of dynamic viscosity in the centimeter gram second system of units.

Example 6—Storage Stability Test

The storage stability of the suspension has been tested over a 6-month storage period under accelerated conditions 40° C. and 75% RH for a period of 6 months and for 24 months at 25° C. and 60% RH. Sufficient bottles of 236 mL bottles were stored at these conditions At each time point of the stability program the composition of suspension was analyzed by HPLC chromatography and the amount of quetiapine fumarate and its known impurities were determined by a validated HPLC assay. Other tests such as sedimentation rate or redispersibility, during the storage period.

Example 7—Pharmacokinetics (PK)

Pharmacokinetics (PK) of quetiapine fumarate were obtained after administration of a single dose of oral liquid suspension in a human volunteer, using the following protocols.

1.1.1 Synopsis of Pilot PK Study
1.0 Protocol Summary—Pilot Study—Fasting Condition

| | | |
|---|---|---|
| Study Title | An open-label, randomized, balanced, single dose, two-treatment, two-period, two-sequence, two-way cross-over, oral bioavailability study of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets 50 mg Distributed by AstraZeneca Pharmaceuticals LP Wilmington, DE 19850 in healthy, adult, human, subjects under fasting conditions. | |
| Study Objectives | 1. | To compare the oral bioavailability of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets 50 mg Distributed by AstraZeneca Pharmaceuticals LP Wilmington, DE 19850 in healthy, adult, human, subjects under fasting conditions. |
| | 2. | To evaluate subject safety and tolerability of investigational products. |
| Study Design | An open-label, randomized, balanced, single dose, two-treatment, two-period, two-sequence, two-way cross-over, oral bioequivalence study in 18 healthy, adult, human subjects under fasting conditions. | |
| Number of Subjects | 18 healthy, adult, human subjects wall be enrolled in to the study. One additional subject will be enrolled to compensate any withdrawn/dropout prior to the dosing of Period-1. If any subject withdrawn/dropout due to any reason prior to the dosing in Period-I, he/she wall be replaced with the additional enrolled subject to ensure the dosing of 18 subjects as per in-house SOP. | |
| Investigational Drug Products | Test (T) | Quetiapine fumarate oral suspension 50 mg/mL Manufactured by: OWP Pharmaceuticals, Inc, 400 East Diehl Road, Suite 400, Naperville, IL 60563 |
| | Reference (R) | SEROQUEL ® (quetiapine fumarate) tablets, 50 mg Distributed by: AstraZeneca Pharmaceuticals LP Wilmington, DE 19850. |
| Washout Period | At least 07 days, between each drug administration. | |
| Duration of the period | The minimum duration of this study wall be at least 11 days (including a gap of washout period of 07 days between each period of the study). | |
| Drug Administration | Subjects should comply at least 10.00 hours overnight fasting prior to drug administration and no food will be allowed at least 4.00 hrs post dose in each period. As per the randomization schedule subject will receive Test or reference product in each period. Reference Product Administration: Single oral dose of reference product [SEROQUEL ® (quetiapine fumarate) tablets, 50 mg] will be administrated to the subject with 240 ± 02 mL of drinking water at room temperature in sitting posture, under fasting conditions. Subjects will be instructed not to chew or crush the tablet and swallow as a whole Test product Administration: 01 mL of test product (Quetiapine fumarate oral suspension 50 mg/mL) will be administered orally to the subjects using a disposable graded syringe at ambient temperature in sitting posture, under fasting condition. After subjects swallow oral suspension, the drug-dispensing container (syringe) will be rinsed with an adequate amount of water (from the given 240 ± 2 mL of water used for drug administration) till it is free of medicine and allowed to swallow the rinse and the remaining amount of drinking water from 240 ± 02 mL will be administered at room temperature in sitting posture, under fasting condition. Subjects will be instructed do not spit the suspension and swallow entirely (as a whole dosage). The clinical staff will ensure that the study participant has swallowed the medication by performing mouth check using torchlight and Spatula/tongue depressor. The clock time when each dose is administered will be recorded on the Case Report Forms. Each subject will receive Test (T) treatment once and Reference (R) treatment once as per randomization crossover design by the end of the study. | |

| | |
|---|---|
| Admission and Stay | Study participants will be housed in the Clinical Pharmacology Unit (CPU) from at least 11.00 hours before drug administration to 48.00 hours after drug administration. |
| Additional Vitals | Orthostatic vitals will be measured at 3.00 and 6.00 hrs post dose (Within ± 45 minutes variation). |

Sample Management

| | |
|---|---|
| Sampling Time Points | In each period, total 21 (1 × 4 mL) blood samples will be collected as per the following schedule: Pre dose (0.00 hour) sample will be collected within 01 hour prior to drug administration and the post dose samples will be collected at 0.25, 0.50, 0.75, 1.00, 1.25, 1.50, 1.75, 2.00, 2.50, 3.00, 3.50 4.00, 5.00, 6.00, 7.00, 8.00, 10.00, 12.00, 16.00 and 24.00 hours in to 4 mL $K_2$EDTA vacutainers.<br>In-house  Ambulatory  Total<br>21  00  21 |
| Blood Loss | Screening — Up to 12 mL<br>Study — 168 mL<br>Discarding the Saline mixed blood — Up to 19 mL<br>Post Study — Up to 12 mL<br>Serum pregnancy test (for females only) — Up to 08 mL<br>Total — Approximately 211 mL for male subjects and 219 mL for female subjects. |
| Anticoagulant | $K_2$EDTA |
| Centrifugation Details | 3800 RPM for 10 minutes at 4° C. ± 2° C. |
| Sample Storage Conditions | Plasma samples will be stored at −70° C. ± 15° C. until drawn for bioanalysis. |
| No. of Aliquots | Two |
| Analytical Methods | The plasma concentration of Quetiapine will be analyzed using a validated bio analytical method(s) by using LC-MS-/MS. |
| Pharmacokinetic Parameters | Primary Parameters: $C_{max}$ $AUC_{0-t}$ and $AUC_{0-inf}$<br>Secondary Parameters: $T_{max}$, $K_{el}$ and $t_{1/2}$. |
| Bioequivalence Criteria | Based on the Analysis, Bioequivalence is declared if the Test products (T) and Reference (R) ratios of the geometric least squares means for ln-transformed pharmacokinetic parameters $C_{max}$, $AUC_{0-t}$ and $AUC_{0-inf}$ and their 90% confidence intervals are within 80.00%-125.00% for Quetiapine. |
| Ethical Issues | The study will commence only after a written approval is obtained from the Ethics Committee (EC). The study will be conducted as per New Drugs and Clinical Trials Rules 2019 G.S.R 227(E) dated: 19 Mar. 2019; Ethical Guidelines for Biomedical Research on Human Participants, Good Clinical Laboratory Practice (GCLP), ICMR (Indian Council of Medical Research; 2017), Declaration of Helsinki (64th WMA General Assembly, Fortaleza, Brazil, October 2013), ICH E6 R2 (Step 5) 'Guidance on Good Clinical Practice', Guidance for Industry Bioavailability and Bioequivalence Studies for Orally Administered Drug Products - General Considerations - U.S. Department of Health and Human Service Food and Drug Administration, Center for Drug Evaluation and Research (CDER) March 2003; 21 CFR (Code of Federal Regulations) and all other applicable regulatory requirements. |

2.0 Protocol Summary—Pilot Study—Food Effect

| | |
|---|---|
| Study Title | An open label, balanced, randomized, single dose, three treatment, three period, three sequence, crossover, oral food effect and fasting comparative bioavailability study of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets, 50 mg Distributed by Astra Zeneca Pharmaceuticals LP Wilmington, DE 19850 in healthy, adult, human subjects. |
| Study Objectives | 1. To compare the oral bioavailability of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets, 50 mg Distributed by AstraZeneca Pharmaceuticals LP Wilmington, DE 19850 in healthy, adult, human, subjects under fasting condition.<br>2. To evaluate the effect of food on the rate and extent of absorption of Quetiapine fumarate oral suspension 50 mg/mL Manufactured by OWP Pharmaceuticals, Inc, 400 East Diehl Road, Suite 400, Naperville, IL 60563 in healthy adult human subjects under fasting/fed condition. |

-continued

| | |
|---|---|
| | 3. To evaluate the subject safety and tolerability of investigational products. |
| Study Design | An open label, balanced, randomized, single dose, three treatment, three period, three sequence, crossover, oral food effect and fasting comparative bioavailability study in 24 healthy, adult, human subjects. |
| Number of Subjects | 24 healthy, adult, human subjects will be enrolled in to the study. Two additional subjects will be enrolled to compensate any withdrawn/dropout prior to the dosing of Period-I. If any subject withdrawn/dropout due to any reason prior to the dosing in Period-I, he/she will be replaced with the additional enrolled subjects to ensure the dosing of 24 subjects as per in-house SOP. |
| Investigational Drug Products | Test (T) Quetiapine fumarate oral suspension 50 mg/mL Manufactured by: OWP Pharmaceuticals, Inc, 400 East Diehl Road, Suite 400, Naperville, IL 60563<br>Reference (R) SEROQUEL ® (quetiapine fumarate) tablets, 50 mg Distributed by: Astra Zeneca Pharmaceuticals LP Wilmington, DE 19850. |
| Washout Period | At least 07 days, between each drug administration. |
| Duration of the period | The minimum duration of this study will be at least 18 days (including a gap of washout period of 07 days between each period of the study). |
| Drug Administration | Subjects require at least 10.00 hours overnight fasting Prior to drug administration for fasting conditions and 10.00 hrs overnight fasting prior to consumption of high fat and high calorie breakfast for fed conditions. No food will be allowed until 4.00 hr post dose.<br>Treatment A: Test product in Fasting condition<br>Treatment B: Test product in Fed condition<br>Treatment C: Reference product in Fasting condition<br>Treatment A administration: 01 mL of Test product (Quetiapine fumarate oral suspension 50 mg/mL) will be administered orally to the subjects using disposable graded syringe at ambient room temperature as per the randomization schedule under fasting condition<br>Treatment B administration: 01 mL of Test product (Quetiapine fumarate oral suspension 50 mg/mL) will be administered orally to the subjects using disposable graded syringe at ambient room temperature as per the randomization schedule under fed condition. After subjects swallowing of oral suspension, the drug-dispensing container (syringe) will be rinsed with an adequate amount of water (from the given 240 ± 2 mL of water used for drug administration) till it is free of medicine and allowed to swallow the rinse and the remaining amount of drinking water from 240 ± 02 mL will be administered at room temperature in sitting posture.<br>Subjects will be instructed not to spit the suspension and swallow as a whole.<br>Treatment C administration: One tablet (SEROQUEL ® (quetiapine fumarate) tablets, 50 mg) of reference product will be administered orally to the subjects in sitting posture with 240 ± 2 mL of water, at ambient room temperature in each period as per the randomization schedule under fasting condition.<br>Subjects will be instructed not to chew or crush the tablet and swallow as a whole.<br>The clinical staff will ensure that the study participant has swallowed the medication by performing mouth check using torchlight and Spatula/tongue depressor. The clock time when each dose is administered will be recorded on the Case Report Forms.<br>Each subject will receive Test treatment A (fasting condition) once Test treatment B (Fed Condition) Once and Treatment C (Reference fasting condition) once as per randomization schedule. |
| Admission and Stay | Study participants will be housed in the Clinical Pharmacology Unit (CPU) from at least 11.00 hours before drug administration to 48.00 hours after drug administration. |
| Additional Vitals | Orthostatic vitals will be measured at 3.00 and 6.00 hrs post dose (Within ± 45 minutes variation). |

Sample Management

| | |
|---|---|
| Sampling Time Points | In each period, total 21 (1 × 4 mL) blood samples will be collected as per the following schedule:<br>Pre dose (0.00 hour) sample will be collected within 01 hour prior to drug administration and the post dose samples will be collected at 0.25, 0.50, 0.75, 1.00, 1.25, 1.50, 1.75, 2.00, 2.50, 3.00, 3.50 4.00, 5.00, 6.00, 7.00, 8.00, 10.00, 12.00, 16.00 and 24.00 hours in to 4 mL $K_2EDTA$ vacutainers. |

| | In-house | Ambulatory | Total |
|---|---|---|---|
| | 21 | 00 | 21 |

| | | |
|---|---|---|
| Blood Loss | Screening | Up to 12 mL |
| | Study | 252 mL |
| | Discarding the Saline mixed blood | Up to 29 mL |
| | Post Study | Up to 12 mL |
| | Serum pregnancy test | Up to 12 mL |

| | | |
|---|---|---|
| | (for females only) | |
| | Total | Approximately 305 mL for male subjects and 317 mL for female subjects |
| Anticoagulant | $K_2EDTA$ | |
| Centrifugation Details | 3800 RPM for 10 minutes at 4° C. ± 2° C. | |
| Sample Storage Conditions | Plasma samples will be stored at −70° C. ± 15° C. until drawn for bioanalysis. | |
| No. of Aliquots | Two | |
| Analytical Methods | The plasma concentration of Quetiapine will be analyzed using a validated bio analytical method(s) by using LC-MS-/MS. | |
| Pharmacokinetic Parameters | Primary Parameters: $C_{max}$, $AUC_{0-t}$ and $AUC_{0-inf}$<br>Secondary Parameters: $T_{max}$, $K_{el}$ and $t_{1/2}$. | |
| Criteria for Evalutation | Based on the statistical results of 90% confidence interval for the ratio of the geometric least squares mean for log-transformed pharmacokinetic parameters $C_{max}$, $AUC_{0-t}$ and $AUC_{0-inf}$ for Quetiapine conclusion will be drawn for treatment A versus treatment B and treatment A versus treatment C.<br>The 90% confidence intervals of the ratio (fed/fasting) of LSM for $C_{max}$, $AUC_{0-t}$ and $AUC_{0-inf}$ of Test product (Quetiapine) will form the basis for concluding the significant/impact of food effect of Quetiapine oral suspension under fasting and fed conditions (A Vs B).<br>If the point estimate of the ratio and the confidence intervals are entirely included in the range of 80.00%-125.00% for $C_{max}$, $AUC_{0-t}$ and $AUC_{0-inf}$ for the log-transformed data, then an absence of food effect on the bioavailability of Quetiapine oral suspension may be indicated.<br>The test product will be concluded bioequivalent to the reference product under fasting condition (A Vs C) if the limit falls within acceptance range (80.00%-125.00%) of the 90% confidence intervals for the difference of means of log-transformed ($C_{max}$, $AUC_{0-t}$ and $AUC_{0-inf}$) with respect to Quetiapine. | |

1.0 Pivotal Study—Protocol Summary—Fasting Study

| | | |
|---|---|---|
| Study Title | An open label, balanced, randomized, single dose, two-treatment, two period, two-sequence, two-way cross-over, oral bioavailability study of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets, 50 mg Distributed by AstraZeneca Pharmaceuticals LP Wilmington, DE 19850 in healthy, adult, human subjects under fasting conditions. | |
| Study Objectives | 4. To compare the oral bioavailability of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets, 50 mg Distributed by AstraZeneca Pharmaceuticals LP Wilmington, DE 19850 in healthy, adult, human, subjects under fasting conditions.<br>5. To evaluate the subject safety and tolerability of investigational products. | |
| Study Design | An open label, randomized, balanced, single dose, two-treatment, two-period, two-sequence, two-way cross-over, oral bioequivalence study in 52 healthy, adult, human subjects under fasting conditions. | |
| Number of Subjects | Fifty two (52) healthy, adult, human subjects will be enrolled in to the study.<br>Two additional subjects will be enrolled to compensate any withdrawn/dropout prior to the dosing of Period-I. If any subject withdrawn/dropout due to any reason prior to the dosing in Period-I, he/she will be replaced with the additional enrolled subject to ensure the dosing of 52 subjects as per in-house SOP. | |
| Investigational Drug Products | Test (T) | Quetiapine fumarate oral suspension 50 mg/mL Manufactured by: OWP Pharmaceuticals, Inc, 400 East Diehl Road, Suite 400, Naperville, IL 60563 |
| | Reference (R) | SEROQUEL ® (quetiapine fumarate) tablets, 50 mg Distributed by: AstraZeneca Pharmaceuticals LP Wilmington, DE 19850. |
| Washout Period | At least 07 days, between each drug administration. | |
| Duration of the period | The minimum duration of this study will be at least 11 days (including a gap of washout period of 07 days between each period of the study). | |
| Drug Administration | Subjects should comply at least 10.00 hours overnight fasting prior to drug administration and no food will be allowed at least 4.00 hrs post dose in each period.<br>As per the randomization schedule subject will receive Test or reference product in each period. | |

| | |
|---|---|
| | Reference Product Administration:<br>Single oral dose of reference product [SEROQUEL ® (quetiapine fumarate) tablets, 50 mg] will be administered to the subject with 240 ± 02 mL of drinking water at room tepmerature in sitting posture, under fasting conditions.<br>Subjects will be instructed not to chew or crush the tablet and swallow as a whole<br>Test product Administration:<br>01 mL of test product (Quetiapine fumarate oral suspension 50 mg/mL) will be administered orally to the subjects using a disposable graded syringe at ambient temperature in sitting posture, under fasting condition.<br>After subjects swallow oral suspension, the drug-dispensing container (syringe) will be rinsed with an adequate amount of water (from the given 240 ± 2 mL of water used for drug administration) till it is free of medicine and allowed to swallow the rinse and the remaining amount of drinking water from 240 ± 02 mL will be administered at room temperature in sitting posture, under fasting condition.<br>Subjects will be instructed do not spit the suspension and swallow as a whole.<br>The clinical staff will ensure that the study participant has swallowed the medication by performing mouth check using torchlight and Spatula/tongue depressor. The clock time when each dose is administered will be recorded on the Case Report Forms.<br>Each subject will receive Test (T) treatment once and Reference (R) treatment once as per randomization crossover design by the end of the study. |
| Admission and Stay | Study participants will be housed in the Clinical Pharmacology Unit (CPU) from at least 11.00 hours before drug administration to 48.00 hours after drug administration. |
| Additional Vitals | Orthostatic vitals will be measured at 3.00 and 6.00 hrs post dose (Within ± 45 minutes variation). |
| | Sample Management |
| Sampling Time Points | In each period, total 21 (1 × 4 mL) blood samples will be collected as per the following schedule:<br>Pre dose (0.00 hour) sample will be collected within 01 hour prior to drug administration and the post dose samples will be collected at 0.25, 0.50, 0.75, 1.00, 1.25, 1.50, 1.75, 2.00, 2.50, 3.00, 3.50 4.00, 5.00, 6.00, 7.00, 8.00, 10.00, 12.00, 16.00 and 24.00 hours in to 4 mL $K_2$EDTA vacutainers. |

| | In-house | Ambulatory | Total |
|---|---|---|---|
| | 21 | 00 | 21 |
| Blood Loss | Screening | | Up to 12 mL |
| | Study | | 168 mL |
| | Discarding the Saline mixed blood | | Up to 19 mL |
| | Post Study | | Up to 12 mL |
| | Serum pregnancy test<br>(for females only) | | Up to 08 mL |
| | Total | | Approximately 211 mL for male subjects and 219 mL for female subjects. |

| | |
|---|---|
| Anticoagulant | $K_2$EDTA |
| Centrifugation Details | 3800 RPM for 10 minutes at 4° C. ± 2° C. |
| Sample Storage Conditions | Plasma samples will be stored at −70° C. ± 15° C. until drawn for bioanalysis. |
| No. of Aliquots | Two |
| Analytical Methods | The plasma concentration of Quetiapine will be analyzed using a validated bio analytical method(s) by using LC-MS-/MS. |
| Pharmacokinetic Parameters | Primary Parameters: $C_{max}$ $AUC_{0-t}$ and $AUC_{0-inf}$<br>Secondary Parameters: $T_{max}$, $K_{el}$ and $t_{1/2}$. |
| Bioequivalence Criteria | Based on the Analysis, Bioequivalence is declared if the Test products (T) and Reference (R) ratios of the geometric least squares means for ln-transformed pharmacokinetic parameters $C_{max}$, $AUC_{0-t}$ and $AUC_{0-inf}$ and their 90% confidence intervals are within 80.00%-125.00% for Quetiapine. |
| Ethical Issues | The study will commence only after a written approval is obtained from the Ethics Committee (EC). The study will be conducted as per New Drugs and Clinical Trials Rules 2019 G.S.R 227(E) dated: 19 Mar. 2019; Ethical Guidelines for Biomedical Research on Human Participants, Good Clinical Laboratory Practice (GCLP), ICMR (Indian Council of Medical Research; 2017), Declaration of Helsinki (64th WMA General Assembly, Fortaleza, Brazil, October 2013), ICH E6 R2 (Step 5) 'Guidance on Good Clinical Practice', Guidance for Industry Bioavailability and Bioequivalence Studies for Orally Administered Drug Products-General Considerations-U.S. Department of Health and Human Service Food and Drug Administration, Center for Drug Evaluation and Research (CDER) |

-continued

March 2003; 21 CFR (Code of Federal Regulations) and all other applicable regulatory requirements.

3.0 Pivotal Study Protocol Summary—Food Effect Study

| | |
|---|---|
| Study Title | An open label, balanced, randomized, single dose, three treatment, three period, three sequence, crossover, oral food effect and fasting comparative bioavailability study of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets, 50 mg Distributed by Astra Zeneca Pharmaceuticals LP Wilmington, DE 19850 in healthy, adult, human subjects. |
| Study Objectives | 6. To compare the oral bioavailability of Quetiapine fumarate oral suspension 50 mg/mL Manufactured by OWP Pharmaceuticals, Inc, 400 East Diehl Road, Suite 400, Naperville, IL 60563 with SEROQUEL ® (quetiapine fumarate) tablets, 50 mg Distributed by AstraZeneca Pharmaceuticals LP Wilmington, DE 19850 in healthy, adult, human, subjects under fasting condition.<br>7. To evaluate the effect of food on the rate and extent of absorption of Quetiapine fumarate oral suspension 50 mg/mL Manufactured by OWP Pharmaceuticals, Inc, 400 East Diehl Road, Suite 400, Naperville, IL 60563 in healthy adult human subjects under fasting/fed condition.<br>8. To evaluate the subject safety and tolerability of investigational products. |
| Study Design | An open label, balanced, randomized, single dose, three treatment, three period, three sequence, crossover, oral food effect and fasting comparative bioavailability study in 24 healthy, adult, human subjects. |
| Number of Subjects | 24 healthy, adult, human subjects will be enrolled in to the study. Two additional subjects will be enrolled to compensate any withdrawn/dropout prior to the dosing of Period-I. If any subject withdrawn/dropout due to any reason prior to the dosing in Period-I, he/she will be replaced with the additional enrolled subjects to ensure the dosing of 24 subjects as per in-house SOP. |
| Investigational Drug Products | Test (T) Quetiapine fumarate oral suspension 50 mg/mL Manufactured by: OWP Pharmaceuticals, Inc, 400 East Diehl Road, Suite 400, Naperville, IL 60563<br>Reference (R) SEROQUEL ® (quetiapine fumarate) tablets, 50 mg Distributed by: Astra Zeneca Pharmaceuticals LP Wilmington, DE 19850. |
| Washout Period | At least 07 days, between each drug administration. |
| Duration of the period | The minimum duration of this study will be at least 18 days (including a gap of washout period of 07 days between each period of the study). |
| Drug Administration | Subjects require at least 10.00 hours overnight fasting Prior to drug administration for fasting conditions and 10.00 hrs overnight fasting prior to consumption of high fat and high calorie breakfast for fed conditions. No food will be allowed until 4.00 hr post dose.<br>Treatment A: Test product in Fasting condition<br>Treatment B: Test product in Fed condition<br>Treatment C: Reference product in Fasting condition<br>Treatment A administration: 01 mL of Test product (Quetiapine fumarate oral suspension 50 mg/mL) will be administered orally to the subjects using disposable graded syringe at ambient room temperature as per the randomization schedule under fasting condition<br>Treatment B administration: 01 mL of Test product (Quetiapine fumarate oral suspension 50 mg/mL) will be administered orally to the subjects using disposable graded syringe at ambient room temperature as per the randomization schedule under fed condition. After subjects swallowing of oral suspension, the drug-dispensing container (syringe) will be rinsed with an adequate amount of water (from the given 240 ± 2 mL of water used for drug administration) till it is free of medicine and allowed to swallow the rinse and the remaining amount of drinking water from 240 ± 02 mL will be administered at room temperature in sitting posture.<br>Subjects will be instructed not to spit the suspension and swallow as a whole.<br>Treatment C administration: One tablet (SEROQUEL ® (quetiapine fumarate) tablets, 50 mg) of reference product will be administered orally to the subjects in sitting posture with 240 ± 2 mL of water, at ambient room temperature in each period as per the randomization schedule under fasting condition.<br>Subjects will be instructed not to chew or crush the tablet and swallow as a whole. |

-continued

| | |
|---|---|
| | The clinical staff will ensure that the study participant has swallowed the medication by performing mouth check using torchlight and Spatula/tongue depressor. The clock time when each dose is administered will be recorded on the Case Report Forms. Each subject will receive Test treatment A (fasting condition) once Test treatment B (Fed Condition) Once and Treatment C (Reference fasting condition) once as per randomization schedule. |
| Admission and Stay | Study participants will be housed in the Clinical Pharmacology Unit (CPU) from at least 11.00 hours before drug administration to 48.00 hours after drug administration. |
| Additional Vitals | Orthostatic vitals will be measured at 3.00 and 6.00 hrs post dose (Within ± 45 minutes variation). |
| | Sample Management |
| Sampling Time Points | In each period, total 21 (1 × 4 mL) blood samples will be collected as per the following schedule: Pre dose (0.00 hour) sample will be collected within 01 hour prior to drug administration and the post dose samples will be collected at 0.25, 0.50, 0.75, 1.00, 1.25, 1.50, 1.75, 2.00, 2.50, 3.00, 3.50 4.00, 5.00, 6.00, 7.00, 8.00, 10.00, 12.00, 16.00 and 24.00 hours in to 4 mL K$_2$EDTA vacutainers. |
| | In-house     Ambulatory     Total<br>21           00            21 |
| Blood Loss | Screening                           Up to 12 mL<br>Study                                252 mL<br>Discarding the Saline mixed blood     Up to 29 mL<br>Post Study                        Up to 12 mL<br>Serum pregnancy test          Up to 12 mL<br>(for females only)<br>Total                                Approximately 305 mL for male subjects and 317 mL for female subjects |
| Anticoagulant | K$_2$EDTA |
| Centrifugation Details | 3800 RPM for 10 minutes at 4° C. ± 2° C. |
| Sample Storage Conditions | Plasma samples will be stored at −70° C. ± 15° C. until drawn for bioanalysis. |
| No. of Aliquots | Two |
| Analytical Methods | The plasma concentration of Quetiapine will be analyzed using a validated bio analytical method(s) by using LC-MS-/MS. |
| Pharmacokinetic Parameters | Primary Parameters: $C_{max}$ AUC$_{0-t}$ and AUC$_{0-inf}$<br>Secondary Parameters: $T_{max}$, $K_{el}$ and $t_{1/2}$. |
| Criteria for Evalutation | Based on the statistical results of 90% confidence interval for the ratio of the geometric least squares mean for log-transformed pharmacokinetic parameters $C_{max}$, AUC$_{0-t}$ and AUC$_{0-inf}$ for Quetiapine conclusion will be drawn for treatment A versus treatment B and treatment A versus treatment C.<br>The 90% confidence intervals of the ratio (fed/fasting) of LSM for $C_{max}$, AUC$_{0-t}$ and AUC$_{0-inf}$ of Test product (Quetiapine) will form the basis for concluding the significant/impact of food effect of Quetiapine oral suspension under fasting and fed conditions (A Vs B).<br>If the point estimate of the ratio and the confidence intervals are entirely included in the range of 80.00%-125.00% for $C_{max}$, AUC$_{0-t}$ and AUC$_{0-inf}$ for the log-transformed data, then an absence of food effect on the bioavailability of Quetiapine oral suspension may be indicated.<br>The test product will be concluded bioequivalent to the reference product under fasting condition (A Vs C) if the limit falls within acceptance range (80.00%-125.00%) of the 90% confidence intervals for the difference of means of log-transformed ($C_{max}$, AUC$_{0-t}$ and AUC$_{0-inf}$) with respect to Quetiapine. |

Timetable of Events (Example)

The following is a representative time schedule for one subject assuming that the study medication will be administered at 08:00. A wash out period of 07 days will be maintained between each drug administration. Timings for other subjects will be uniformly staggered:

| DAY | TIME RELATIVE TO DOSING (HOURS) | APPROXIMATE TIME | EVENTS |
|---|---|---|---|
| 1 | −24.00 to −11.00 | 08:00 to 21:00 | Compliance Assessment, Check-In and Dinner. |
| 1 | −10.00 to −9.00 | 22:00 to 23:00 | Bed time |

-continued

| DAY | TIME RELATIVE TO DOSING (HOURS) | APPROXIMATE TIME | EVENTS |
|---|---|---|---|
| 2 | −2.50 | 05:30 | Wake up call |
| 2 | −2.00 to 0.00 | 06:00 to 08:00 | Pre dose Vitals, Well-being and Cannulation |
| 2 | −1.00 | 07:00 | Water restriction begins |
| 2 | −1.00 to 0.00 | 07:00 to 08:00 | Pre-dose blood sample collection |
| 2 | −0.50 | 07:30 | High fat and high calorie breakfast (Only for fed condition) |
| 2 | 0.00 | 08:00 | Dosing & Posture restriction begins. |
| 2 | 0.25 | 08:15 | Blood sample collection |
| 2 | 0.50 | 08:30 | Blood sample collection |
| 2 | 0.75 | 08:45 | Blood sample collection |
| 2 | 1.00 | 09:00 | Blood sample collection, Vitals, Well-being & Water restriction ends. |
| 2 | 1.25 | 09:15 | Blood sample collection |
| 2 | 1.50 | 09:30 | Blood sample collection |
| 2 | 1.75 | 09:45 | Blood sample collection |
| 2 | 2.00 | 10:00 | Blood sample collection |
| 2 | 2.50 | 10:30 | Blood sample collection |
| 2 | 3.00 | 11:00 | Blood sample collection, Orthostatic vitals & Well-being. |
| 2 | 3.50 | 11:30 | Blood sample collection |
| 2 | 4.00 | 12:00 | Blood sample collection and Lunch |
| 2 | 5.00 | 13:00 | Blood sample collection |
| 2 | 6.00 | 14:00 | Blood sample collection, Orthostatic vitals & Well-being |
| 2 | 7.00 | 15:00 | Blood sample collection |
| 2 | 8.00 | 16:00 | Blood sample collection & Posture restriction ends. |
| 2 | 09.00 | 17:00 | Snacks |
| 2 | 10.00 | 18:00 | Blood sample collection, Vitals & Well-being |
| 2 | 12.00 | 20:00 | Blood sample collection |
| 2 | 13:00 | 21:00 | Dinner |
| 3 | 16.00 | 00:00 | Blood sample collection |
| 3 | 24.00 | 08:00 | Blood sample collection, Vitals & Well-being |
| 3 | 25.00 | 09:00 | Breakfast |
| 3 | 28.00 | 12:00 | Vitals & Well-being |
| 3 | 29.00 | 13:00 | Lunch |
| 3 | 33.00 | 17:00 | Snacks |
| 3 | 36.00 | 20:00 | Vitals & Well-being |
| 3 | 37.00 | 21:00 | Dinner |
| 4 | 48.00 | 08:00 | Vitals, Well-being, Check out and Post study assessment. |

Note:
Actual time may change according to the dose administration time.

Note: Actual time may change according to the dose administration time.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the Applicant.

What is claimed is:

1. A method for treating a mental disorder in a human subject, the method comprising orally administering to the human subject suffering from the mental disorder an effective amount of an oral liquid suspension comprising:
28.83 mg/ml of quetiapine fumarate;
1 mg/ml of methylparaben;
0.3 mg/ml of sodium benzoate;
0.8 mg/ml of saccharin sodium dihydrate;
0.3 mg/ml of sodium phosphate dibasic;
30 mg/ml of a sorbitol solution;
22.5 mg/ml of propylene glycol;
50 mg/ml of glycerin;
12.6 mg/ml of silicified microcrystalline cellulose;
1.8 mg/ml of carboxymethylcellulose sodium;
1.8 mg/ml of xanthan gum;
787.046 mg/ml of purified water;
6 mg/ml of poloxamer 188;
50 mg/ml of polyethylene glycol 400; and
5 mg/ml of sucralose.

2. The method of claim 1, wherein the mental disorder comprises at least one of Schizophrenia, Bipolar I disorder manic episodes, and Bipolar disorder depressive episodes.

3. The method of claim 1, wherein the effective amount of the oral liquid suspension ranges from 0.1 ml to 50.0 ml.

4. The method of claim 1, wherein the effective amount of the oral liquid suspension comprises from 25 mg to 400 mg of quetiapine fumarate.

5. The method of claim 1, wherein the effective amount of the oral liquid suspension comprises 25 mg, 50 mg, 100 mg, 200 mg, 300 mg, or 400 mg of quetiapine fumarate.

6. The method of claim 1, wherein the oral liquid suspension provides maximum plasma concentrations of the quetiapine in blood in less than 1.5 hours after administration.

7. The method of claim 1, wherein the mental disorder is selected from the group consisting of (i) Schizophrenia in Adults, (ii) Schizophrenia in Adolescents, (iii) Bipolar Mania in Adults Monotherapy or as an adjunct to lithium or divalproex, (iv) Bipolar Mania in Children and Adolescents, Monotherapy, (v) Bipolar Depression in Adults; and any combination thereof.

8. The method of claim 1, wherein relative to a solid oral dosage form containing an equivalent amount of quetiapine fumarate, administration of the oral liquid suspension results in a lower incidence, severity, and/or duration of adverse reactions including at least one of hyperglycemia, dyslipidemia, somnolence, dry mouth, dizziness, constipation, asthenia, abdominal pain, postural hypotension, pharyngitis, weight gain, lethargy, alanine transaminase increased, dyspepsia, fatigue, increased appetite, nausea, vomiting, and tachycardia.

9. The method of claim 1, wherein upon administering under fasted conditions to an adult subject taking no other medications, the oral liquid suspension provides a maximum plasma concentration of quetiapine of 80-120 mcg/mL in less than 1.5 hours; and wherein a half-life of quetiapine in plasma is 7 hours.

10. The method of claim 1, wherein prior to orally administering the oral liquid suspension is subjected to shaking until the ingredients therein are re-dispersed.

11. The method of claim 1, wherein the oral liquid suspension comprises the quetiapine fumarate in particulate form having a particle size wherein at least 90 wt. % of the particles are not more than 60 microns.

12. The method of claim 1, wherein the oral liquid suspension comprises particles, and wherein at least 90 wt. % of the particles are not more than 300 microns, at least 50 wt. % of the particles are not more than 100 microns, and at least 10 wt. % of the particles are not more than 30 microns.

13. The method of claim 1, wherein the oral liquid suspension has a viscosity at 25° C. of 15-40 millipoises.

14. The method of claim 1, wherein the oral liquid suspension has a pH of 5-6.5.

15. The method of claim 1, wherein the oral liquid suspension has a specific gravity of not more than 1.2.

16. The method of claim 1, wherein the oral liquid suspension; is free from microbial growth for at least 24 months under ambient conditions.

17. The method of claim 1, wherein the oral liquid suspension; is free from *Escherichia coli* for at least 24 months under ambient conditions.

18. The method of claim 1, wherein the oral liquid suspension; is free from *Burkholderia cepacia* complex for at least 24 months under ambient conditions.

19. The method of claim 1, wherein the oral liquid suspension is an immediate release dosage form.

20. The method of claim 1, wherein the oral liquid suspension is an immediate release dosage form providing in-vitro dissolution rate of quetiapine fumarate of more than 80% within 20 minutes, when said dosage form is placed in a dissolution vessel filled with 900 ml of deionized water maintained at 37±0.5° C. and stirred at a paddle speed of 50 rpm using a USP Type II apparatus.

21. The method of claim 1, wherein the oral liquid suspension further comprises one or more flavoring agents.

22. The method of claim 1, wherein the oral liquid suspension further comprises cherry flavor, present at a concentration of 2.00 mg/ml.

23. The method of claim 1, wherein the oral liquid suspension further comprises one or more colorants.

24. The method of claim 1, wherein the oral liquid suspension comprises 0.02 mg/ml of FD&C red #40 and 0.002 mg/ml of FD&C yellow #6.

25. The method of claim 1, wherein the oral liquid suspension further comprises 2 mg/ml of cherry flavor, 0.02 mg/ml of FD&C red #40, and 0.002 mg/ml of FD&C yellow #6.

26. A method for treating a mental disorder in a human subject, the method comprising orally administering to the human subject suffering from the mental disorder an effective amount of an oral liquid suspension comprising:

28.83 mg/ml of quetiapine fumarate;
1 mg/ml of methylparaben;
0.3 mg/ml of sodium benzoate;
0.8 mg/ml of saccharin sodium dihydrate;
0.3 mg/ml of sodium phosphate dibasic;
30 mg/ml of a sorbitol solution;
22.5 mg/ml of propylene glycol;
50 mg/ml of glycerin;
12.6 mg/ml of silicified microcrystalline cellulose;
1.8 mg/ml of carboxymethylcellulose sodium;
1.8 mg/ml of xanthan gum;
787.046 mg/ml of purified water;
6 mg/ml of poloxamer 188;
50 mg/ml of polyethylene glycol 400; and
5 mg/ml of sucralose;
wherein,
the mental disorder comprises at least one of Schizophrenia, Bipolar I disorder manic episodes, and Bipolar disorder depressive episodes;
the oral liquid suspension comprises from 25 mg to 400 mg of quetiapine fumarate; has a viscosity at 25° C. of 15-40 millipoises; has a pH of 5-6.5; and has a specific gravity of not more than 1.2; and the effective amount of the oral liquid suspension administered to the human subject ranges from 0.1 ml to 50.0 ml.

* * * * *